United States Patent [19]
Myers et al.

[11] Patent Number: 5,912,413
[45] Date of Patent: Jun. 15, 1999

[54] ISOLATION OF SU1, A STARCH DEBRANCHING ENZYME, THE PRODUCT OF THE MAIZE GENE SUGARY1

[75] Inventors: Alan M. Myers, Ames; Martha Graham James, Des Moines, both of Iowa

[73] Assignee: Iowa State University Research Foundation, Inc., Ames, Iowa

[21] Appl. No.: 08/410,784

[22] Filed: Mar. 24, 1995

[51] Int. Cl.$^6$ .......................... C12N 15/29; C12N 15/82; A01H 4/00; A01H 5/00
[52] U.S. Cl. .................. 800/205; 435/69.1; 435/172.3; 435/320.1; 435/419; 536/236; 536/24.1
[58] Field of Search .......................... 800/205; 435/69.1, 435/172.3, 320.1, 419; 536/23.6, 24.1

[56] References Cited

PUBLICATIONS

Pan, David et al., "A Debranching Enzyme Deficiency in Endosperms of the Sugary–1 Mutants of Maize", *Plant Physiol.* 74: 324–328 (1984).
Creech, Roy G., "Carbohydrate Synthesis in Maize", *Advances in Agronomy*, 20: 275–322 (1968).
Preiss, Jack, "Biology and Molecular Biology of Starch Synthesis and its Regulation", *Oxford Surveys of Plant Molecular and Cell Biology*, 7: 59–114 (1991).
Sumner, James B. et al., "The Water–Soluble Polysaccharides of Sweet Corn", *Archives of Biochemistry*, 4: 7–9 (1944).

*Primary Examiner*—Douglas W. Robinson
*Assistant Examiner*—Thomas Haas
*Attorney, Agent, or Firm*—Weingarten, Schurgin, Gagnebin & Hayes LLP

[57] ABSTRACT

SU1, a starch debranching enzyme active in maize endosperm (*Zea mays*), and the cDNA and gene sequences encoding SU1 are disclosed. The amino acid sequence is significantly similar to that of bacterial isoamylases, enzymes that hydrolyze α-(1→6) glycosidic bonds. Amino acid sequence similarity establishes SU1 as a member of the α-amylase superfamily of starch hydrolytic enzymes. Also disclosed are antibodies reactive with the SU1 protein, methods of producing antibodies to the SU1 protein, methods of producing fusion proteins including SU1 and methods of producing transgenic plants with a modified su1 gene. The expressed SU1 protein can serve as a replacement for the bacterial and fungal enzymes currently used in the starch processing industry.

27 Claims, 17 Drawing Sheets

```
  1  R   L   V   T   H   S   T   R   T   H   Y   L   I   G   Q   S   Q   T   N   W        20
  1  CGTCTCGTCACACACTCCACTCGAACGCCACTACTTGATCGGCCAAAGCCAAACGAACTGG                         60
 21  A   P   S   P   P   L   P   L   P   M   A   Q   K   L   P   C   V   S   S   P        40
 61  GCTCCCTCCCCCTCCACTTCCTCTCCCCATGGCGCAGAAGCTCCCCTGCGTCTCGTCCCG                         120
                                    NcoI
 41  R   P   L   L   A   V   P   A   G   R   W   R   A   G   V   R   G   R   P   N        60
121  CGCCCGCTGCTCGCCGTGCCCGCGGGGCGGTGGCGCGCCGGTGCCGTGCGGGGCCCGGCCCAAT                     180
 61  V   A   G   L   G   R   G   R   L   S   L   H   A   A   A   A   R   P   V   A        80
181  GTGGCGGGACTGGGGCGGGGCCGGTTGTCTCTCCACGCCGCCGCGGCCCGCCCCGTGGCC                         240
 81  E   A   V   Q   A   E   E   D   D   D   D   D   E   E   V   A   E   E   R   *       100
241  GAGGCGGTGCAGGCGGAGGAGGACGACGACGACGACGAGGAGGTGGCCGAGGAGAGG                            300
101  F   A   L   G   G   D   A   C   R   V   L   A   G   M   P   A   P   L   G   A   T   120
301  TTCGCGCTGGGCGGCGACGCCTGCCGGGTGCTCGCGGGAATGCCCGCTCCGCGCCACC                           360
                                                                        NarI
121  A   L   R   G   G   V   N   F   A   V   Y   S   S   G   A   S   A   A   S   L       140
361  GCGCTCCGCGGCGGCGTGAACTTCGCCGTCTACTCCAGCGGTGCCTCCGCCGTCGCTG                           420
                             HincII
141  S   L   F   A   P   G   D   L   K   A   D   R   V   T   E   E   V   P   L   D       160
421  AGCCTCTTCGCTCCCGGCGACCTCAAGGCGGATAGGGTGACCGAGGAGGTGCCCCTCGAT                         480
161  P   L   N   R   T   G   N   V   W   H   V   F   I   H   G   D   E   L   H           180
481  CCCCTGCTCAACCGAACGGGAAACGTGTGGCACGTGTTCATCCACGGGGACGAGCTGCAC                         540
                                              PmlI
```

FIG. 1A

```
181  G   M   L   C   G   Y   R   F   D   G   V   F   A   P   E   R   G   Q   Y   Y                                200
541  GGCATGCTCTGCGGATACAGGTTCGATGGCGTGTTCGCCCCTGAGCGGCGGACAGTACTAC                                                  600
       SphI
201  D   V   S   N   V   V   V   D   P   P   Y   A   K   A   V   V   S   R   G   E   Y                            220
601  GATGTGTCCAACGTTGTGGTGGATCCATACGCTAAGGCAGTGGTGTAAGCCGAGGTGAATAT                                                 660
                                 BamHI
221  G   V   P   A   P   G   G   S   C   W   P   Q   M   A   G   M   I   P   L   P                                240
661  GGTGTGCCTGCGCCTGGTGGTAGTTGTTGGCCTCAAATGGCTGGTATGATCCCTCTTCCC                                                   720
241  Y   N   K   F   D   W   Q   G   D   L   P   L   G   Y   H   Q   K   D   L   V                                260
721  TATAATAAGTTTGATTGGCAAGGTGACCTACCCCTTGGTTACCATCAGAAGGACCTTGTC                                                   780
                                                      KpnI
261  I   Y   E   M   H   L   R   G   F   T   K   H   N   S   K   T   K   H   P                                    280
781  ATATATGAAATGCATTTGCGTGGATTCACAAAGCACAACTCAAGACAAGACAAAACACCCA                                                  840
281  G   T   Y   I   G   A   V   S   K   L   D   H   L   K   E   L   G   V   N   C                                300
841  GGAACTTACATTGGTGCTGTGTCAAAGCTTGACCATCTAAAGGAACTTGGAGTGAACTGT                                                   900
                                       HindIII
301  I   E   L   M   P   C   H   E   F   N   E   L   E   Y   F   S   S   S   S   K                                320
901  ATAGAGCTAATGCCCTGCCATGAGTTCAATGAGCTAGAGTACTTCAGCTCCTCTTCGAAG                                                   960
321  M   N   F   W   G   Y   S   T   I   N   F   F   S   P   M   A   R   Y   S   S                                340
961  ATGAACTTCTGGGGATATTCCACAATAAATTTTTTCTCACCAATGGCAAGATATTCTTCA                                                  1020
341  S   G   I   R   D   S   G   C   G   A   I   N   E   F   F   K   A   F   V   R   E                           360
1021 AGTGGCATAAGAGACTCTGGATGTGGTGCCATAAATGAATTTAAAGCTTTTGTAAGGGAG                                                  1080
                                                                HindIII
361  A   H   K   R   G   I   E   V   I   M   D   V   V   F   N   H   T   A   E   G                                380
1081 GCCCACAAACGGGGAATTGAGGTGATCATGGATGTTGTCTTCAATCATACAGCTGAAGGT                                                  1140
                                       BclI
```

*FIG. 1B*

```
 381  N  E  K  G  P  I  L  S  F  R  G  I  D  N  S  T  Y  Y  M  L      400
1141  AATGAGAAAGGCCCAATATATTATCCTTTAGGGGGATAGATAATAGTACATACTACATGCTT   1200

401  A  P  K  G  E  F  Y  N  Y  S  G  C  G  N  T  F  N  C  N  H      420
1201  GCACCTAAGGGAGAGTTTTATAATTATTCTGGTGTGTGGAAATACCTTCAATTGTAATCAT    1260

421  P  V  V  R  E  F  I  V  D  C  L  R  Y  W  V  T  E  M  H  V      440
1261  CCTGTAGTCCGTGAATTTATAGTGGATTGCTTGAGATACTGGGTAACAGAAATGCATGTT    1320

441  D  G  F  R  F  D  L  A  S  I  L  T  R  G  C  S  L  W  D  P      460
1321  GATGGTTTTCGTTTTGACCTTGCATCTATACTGACCAGAGGATGCAGTCTATGGGATCCA    1380
                                                         BamHI
 461  V  N  V  Y  G  S  P  M  E  G  D  M  I  T  T  G  T  P  L  V      480
1381  GTTAATGTGTATGGAAGTCCAATGGAAGGTGACATGATTACGACAGGGACACCTCTTGTT    1440

481  A  P  P  L  I  D  M  I  S  N  D  P  I  L  G  N  V  K  L  I      500
1441  GCCCCACCACTTATTGACATGATTAGCAATGACCCAATTCTTGGAAATGTCAAGCTCATT    1500

501  A  E  A  W  D  A  G  G  L  Y  Q  E  G  Q  F  P  H  W  N  V      520
1501  GCTGAAGCATGGGATGCAGGAGGTCTCTATCAAGAAGGTCAGTTTCCTCACTGGAACGTT    1560

521  W  S  E  W  N  G  K  Y  R  D  T  V  R  Q  F  I  K  G  T  D      540
1561  TGGTCAGAGTGGAATGGGAAAGTATCGCGATACCGTGCGTCAGTTCATCAAAGGCACAGAT   1620

541  G  F  A  G  A  F  A  E  C  L  C  G  S  P  Q  L  Y  Q  A  G      560
1621  GGATTTGCTGGTGCTTTTGCTGAATGCCTATGTGGAAGTCCACAGTTATACCAGGCAGGG   1680

561  G  R  K  P  W  H  S  I  G  F  V  C  A  H  D  G  F  T  L  A      580
1681  GGGAGGAAGCCTTGGCACAGTATCGGCTTTGTATGTGCACACGATGGATTTACACTGGCT   1740
```

FIG. 1C

```
581   D   L   V   T   Y   N   S   K   Y   N   L   S   N   G   E   D   F   R   D   G          600
1741  GATTTGGTCACATACAATAGCAAGTACAACTTGTCAAATGGTGAGGACTTCAGAGATGGG                          1800

601   E   N   H   N   L   S   W   N   C   G   E   E   G   E   F   A   S   L   S   V          620
1801  GAAAATCATAATCTTAGCTGGAATTGTGGGAGGAGAATTTGCAAGTCTGTCAGTC                                1860

621   R   R   L   R   K   R   Q   M   R   N   F   F   V   C   L   M   V   S   Q   G          640
1861  CGAAGATTAAGGAAGAGGCAAATGCGCAATTTCTTTGTTTGTCTTATGGTTTCTCAGGGA                          1920

641   V   P   M   F   Y   M   G   D   E   Y   G   H   T   K   G   G   N   N   N   T          660
1921  GTTCCAATGTTCTACATGGGCGATGAATATGGTCACACAAGGAGGAACAACAATACG                             1980

661   Y   C   H   D   H   Y   V   N   Y   F   R   W   D   K   K   E   E   Q   S   S          680
1981  TACTGCCATGACCATTATGTCAATTATTTCCGTTGGGATAAGAAGGAAGAACAATCCTCT                          2040

681   D   L   Y   R   F   C   R   L   M   T   E   F   F   R   K   E   C   E   S   L   G      700
2041  GATTTGTACAGATTCTGCCGTCTCATGACCGAATTCCGCAAAGAATGTGAATCTCTTGGC                          2100
                                            EcoRI

701   L   E   D   F   F   P   T   S   E   R   L   K   W   H   G   H   Q   P   G   K   P      720
2101  CTTGAGGACTTCCCGACTTCAGAACGGTTGAAATGGCACGGTCATCAGCCCGGGAAGCCT                          2160

721   D   W   S   E   A   S   R   F   V   A   F   T   M   K   D   E   T   K   G   E          740
2161  GACTGGTCAGAGGCAAGCCGATTCGTTGCCTTCACCATGAAGGACGAAACCAAAGGCGAG                          2220

741   I   Y   V   A   F   N   T   S   H   L   P   V   V   G   L   P   E   R   S              760
2221  ATCTACGTGGCCTTCAACACCAGTCACCTTCCGGTTGTTGGGCTTCCAGAGCGCTCT                              2280
      BglII

761   G   F   R   W   E   P   V   V   D   T   G   K   E   A   P   Y   D   F   L   T          780
2281  GGGTTCCGATGGGAGCCGGTGGTGACACCGGCAAGGAGGCACCATATGACTTCCTCACC                           2340
```

FIG. 1D

```
781  D   G   L   P   D   R   A   V   T   V   V   Y   Q   F   S   H   F   L   N   S   N                  800
2341 GATGGCCTGCCAGATCGTGTCGTCACCGTCTACCAGTTCTCTCATTCCTCAACTCCAAT                                         2400

801  L   Y   P   M   L   S   Y   S   S   I   I   L   V   L   R   P   D   V   *                          
2401 CTCTATCCTATGCTCAGCTACTCCTCCATCATCCTTGTATTGCGCCCCTGATGTCTGAAAG                                       2460

2461 AAGCAGATACAATAGAGTATACTATAGCGGTTGTTCTCTAGGCTGTAGCATGCAGTGGAA                                        2520
                                                            SphI
2521 ACTGGAAAATGTTGGGGTTGCTCTGTTGTCGGTAGTTTACATGCGCATGTCGGTATGTGT                                        2580

2581 ACATAAAGCTGGTGGATCTCAGTTCTCAGATCGGACTCGAGACGGCAAAACCATTGCCAG                                        2640
                                              XhoI
2641 TTGGCTGGTTCTCTGAAGTTTTGTTTGGTGTAAAGAAATGGTGGTCCATCATCTACTCTT                                       2700

2701 TTTTTTTTTTTT  2712
```

*FIG. 1E*

```
  1  GAATTCTCTTTTGAGTTAATTAACCACCCGTACAAATTGAGCAAGCCTTTGTTAT     60
 61  CTCCACATACATGTATATTAATATAAGATACATATCTCGTTTTTTAAAGAAATATCGC  120
121  ATGGGTTTATTATTATTTAAGACTAGTTTGTAAACTCTATTTTCTGAGAAATTCCTA   180
                        SpeI
181  TTTTTCAAGAGAAAATAAACTAATTTATTTGAAAAAATGTAAACTTTTGATAAAATAGG 240
241  ATTGTCAAACTAGACCTTATTATTATATGTATATGTATAAGTATCACTGTGAAAGT    300
301  ATGAAAAAAGTTTAGTTCTTTTCTTTTGGTGAATATAAGAGTATAAATAATAAAAGTGG 360
361  AATAGTATAGTGCCTGAAAAGCGGCAACTAGATCGTGTTGCCAGTACGCGGGCCCCACA 420
421  GAAAAAGCCCACGTCCGCCTCCCCGCTGCCGAAAAACGACACGGGCCCGAGTGGACGACGG 480
481  TGGCCCGACGCAGACGCAGACAGTCCTTCCGGCTGTGAAAAACTGCACATCGTCCGACC 540
                                                         **
541  CGCCGTCCGCCGATCCGAGCGGTCCACTCTGTCAGCTCACTCGATCCGGACCGCC     600
```

FIG. 2A

```
601  CCTCCTCACACCGTGGGCACGGAGCCAAGAGACGAGCGCGTCCTCGGATCCACCTCGT    660
661  CTCGTCACACACTCCACTGAACGCACTACTTGATCGGCCAAAGCCAACGAACTGGGCT    720
721  CCCTCCCCTCCACTTCCTCTCCCCATGGCCAGCAGCTCCCCTGCGTCTCGTGCCGCGC    780
781  CCGCTGCTCGCCGTGCCCGGTGCCCGGGGCCCGGCGTGCGCGGTGCGGGCCAATGTG    840
841  GCGGGACTGGGGCCGGCTGTCTCTCCACGCCGGGCCGCGCCCGTGGCCGAG         900
901  GCGGTGCAGGCGGAGGCGACGACGACGAGGAGTGGCCGAGGAGAGGTTC           960
961  GCGCTGGGGCGGTGCTCGCGGGAATGCCCGGCTCGGGCCACCGCG               1020
            NarI
1021 CTCCGGCGGCGGGTGTCAACTTCGCCGTCTACTCCAGCGGTGCCTCCGCCGTGCTGTGC    1080
           HincII
                                   ##
1081 CTCTTTCGCTCCCGGCGACCTCAAGGCGTGAGCATCCCCACCCCTAGTCTTTGATGAAT    1140
1141 GCAATTTCTGCAACCGGTCTGCTCGGATCCTTCTGTGTCTTCTCTCTTTTGGAATTT    1200
```

*FIG. 2B*

```
1201  GAATGGAAGGAAGTCGGCTTACTAACTTACTCCTCTATTCTCTCTCTCGAATAACT       1260
1261  TGCTTCTCGATGCTGTACGCTAATTGTTGGCTTCATACGATACGCCGGTGCTGAAATGGA  1320
                             ##
1321  CTGAGTTCTCTCTGTATTCCTGGTATGATGCAGGATAGGGTGACCGAGGAGGTGCCCCTCGA 1380
1381  TCCCCTGCTCAACCGAACGGGAAACGTGTGGCACGTGTTCATCCACGGGACCAGCTGCA   1440
                                                       PmlI
1441  CGGCATGCTCTACGGATACAGGTTCGATGCGTGTTCGCCCCCTGAGCGCGGACAGTACTAC 1500
        SphI
1501  GATGTGTCCAACGTGTGGATCCATACGCTAAGGTGACGGGCTGTTGTCTTTACTTT      1560
                       ##
                    BamHI
1561  GGCTATGCGTGTGAGCTGTGACACACTCAGAAACTGATTGCTGGGTGCTTGCTCATGTTT  1620
1621  TAGTTGTTTACTTCTCTCTGTTGTTGTTTTCTCTAGGCAGGCAGTGGTAAGCCGAGGTGA  1680
                                       ##
1681  ATATGGTGTGCCTGGCCTGGTAGTTGTTGGCCTCAAATGGCTGTATGATCCCTCT       1740
1741  TCCCTATAATAAGGTAAGCCAGAACTACTCTCGCTCACACTACCTTCCTGTTTGCTTTCA  1800
                ##
```

*FIG. 2C*

```
1801  TGCTGTATCCTTCTCTTCCAGTTTTATGATCTCCCCATGTCTGACTCACTCACGATTAAA   1860
1861  CAATAAAAAGAAACCACCGCATATATTTGGCTCATTGATGCATTTGAAAAGCTCCGCATG   1920
1921  AACTAACTGAACAAAGCGCCTAGAACTATCAACTGTAGGTTAGGACTCATTGGCTTCTGC   1980
1981  TTACTTAGTTTCTGCCTTTGCCCAGTTCAAATGGAGTCGAAGTTATATTTCACGTGCCTA   2040
                                           **
2041  TTATGTTGTCCTGTATGATAAGGTTGCATTTGCAGTTTGATTGGCAAGGTGACCTACCCT   2100
                                           ##       ‾‾‾‾‾‾‾‾‾‾‾‾‾‾
2101  TGGGTACCACCATCAGAAGGACCTTGTCATATATGAAATGCATTGCGTGGATTCACAAAGCA   2160
      ‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾
      KpnI
2161  CAACTCAAGCAAGACAAAACACCCAGGAACTTACATTGGTGCTGTGTCAAAGCTTGACCA   2220
      ‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾
                                                        HindIII
2221  TCTAAAGGTACTGTTACGAACAGACTAGCTATAAGTCTGCCGAAAGTGTCCTCATGCATTT   2280
      ‾‾‾‾‾‾‾‾‾‾‾
          ##
2281  GTTTAGGTTTTGCAACTATGCCAACTATGCCAAGTAATGCTGCCCTAGTCTATTAGTTCA   2340
2341  TAGGGGCATAAACACAGATTTTACTTTGTGCTTACATAAAATGTTTTTTGCTCAGAACTTG   2400
```

```
2401 CAGTGGTATTGGTCGTCGTCTTAGACTTTTTGGCATGTGTTGTTGTTGGAATATAATATAAG 2460
2461 TGAATTGTCAACCTTCTCCTATCAGCTTAAGCTTTTGGATAGAAAGAATTGGTTGGTGCA 2520
2521 TGTAACTTAATATGGTATTAAAGACAGAGGTCATGAATTC 2560
                                    EcoRI
```

Notes:
1. ** indicates a gap exists between these nucleotides (<200 bp)
2. ## indicates a splice junction
3. ---- under a sequence indicates the sequence in this region is uncertain

FIG. 3A

FIG. 3B

ISOLATION OF SU1, A STARCH DEBRANCHING ENZYME, THE PRODUCT OF THE MAIZE GENE SUGARY1

GOVERNMENT RIGHTS

This invention was made in part with government support under U.S. Department of Agriculture Grant No. 93-37301-8671. The government has certain rights in this invention.

FIELD OF THE INVENTION

This invention relates to nucleic acid sequences encoding the sugary1 (su1) gene from maize, and to the proteins and polypeptides encoded by these sequences.

BACKGROUND OF THE INVENTION

Starch is the major storage carbohydrate in higher plants. The biochemical mechanisms of starch biosynthesis are of interest for understanding fundamental aspects of plant physiology and also for their potential utility in manipulating plant growth for practical purposes. Not only is starch a critical primary source of dietary carbohydrates, but it is also used extensively for various industrial purposes ranging from formation of packaging materials to ethanol production. Despite its wide availability in nature and many industrial applications, the mechanisms by which starch is formed in plant endosperm tissue are not well understood.

Starch consists essentially of a mixture of the homopolysaccharides amylose and amylopectin. Amylose is a linear chain of glucosyl units joined by $\alpha$-(1→4) glycosidic bond and normally constitutes about 25% of the total endosperm starch in maize (*Zea mays*). Amylopectin comprises many linear chains of glucosyl monomers joined by $\alpha$-(1→4) linkages and constitutes approximately 75% of the starch. The chains of amylopectin are joined to each other by $\alpha$-(1→6) glycosidic bonds, often referred to as branch linkages.

Sugary1 (su1) is one of the oldest known mutations of maize and has been utilized as a sweet corn variety in North America since the 1700s. Phenotypically, immature mutant kernels with the su1 gene mutations accumulate sucrose and other simple sugars, including phytoglycogen (Black et al., 1966; Evensen and Boyer, 1986), which gives corn its desirable sweetness. Specific efforts to improve particular varieties of sweet corn date back to the middle of the nineteenth century. More recently, Sumner and Somers reported in 1944 that the principal polysaccharide storage product in su1 endosperm was a high molecular weight polysaccharide they called phytoglycogen. In 1958, Erlander proposed that phytoglycogen was a normal intermediate in the process of starch synthesis and that a debranching enzyme removed some of the branches by hydrolyzing the $\alpha$-1,6 branch points.

Phytoglycogen resembles amylopectin in the respect that $\alpha$-(1→4)-linked chains are joined by $\alpha$-(1→6) branch linkages, but the ratio of $\alpha$-(1→6) to $\alpha$-(1→4) linkages is significantly higher in phytoglycogen than it is in amylopectin (Manners, 1985). Although it has been suggested that the su1 gene codes for a starch debranching enzyme (Pan and Nelson, 1984), three different protein isoforms, each with a different level of glycosidase activity, were observed. It is not clear whether this observation was due to differential posttranslational modifications of the proteins, or whether the active enzyme is a multimer which requires combination with products of other gene loci. Further investigation into the mechanisms of starch biosynthesis in plants would be desirable.

SUMMARY OF THE INVENTION

The invention is based on the discovery of a maize endosperm cDNA that encodes a novel starch debranching enzyme, termed SU1. The su1 gene produces a mRNA transcript of approximately 2.8 kb in kernels which includes a continuous open reading frame of 789 codons. The amino acid sequence deduced from the nucleotide sequence is significantly similar to that of bacterial isoamylases, enzymes that hydrolyze $\alpha$-(1→6) glycosidic bonds. Amino acid sequence similarity establishes SU1 as a member of the $\alpha$-amylase superfamily of starch hydrolytic enzymes, and indicates that SU1 is a starch debranching enzyme active in maize endosperm.

cDNA sequences encoding the SU1 protein or portions thereof can be incorporated into replicable expression vectors and the vectors transfected into an appropriate host (e.g., bacterial, yeast, eucaryotic cell culture). Alternatively, genomic DNA fragments encoding the SU1 protein can be utilized in situ. The expressed SU1 protein can be used as a replacement for the bacterial and fungal enzymes currently used in the starch processing industry. Also, the expressed products can be employed as immunogens in order to raise antibodies against SU1. Antibodies reactive with the SU1 protein show that SU1 is expressed in wild type maize endosperm tissue.

Thus, the invention generally features nucleic acid isolates encoding starch debranching enzyme, SU1, or portions thereof; the encoded SU1 protein or portions thereof; methods of producing SU1 or portions thereof; cells transformed with a recombinant vector containing the su1 gene; antibodies to the SU1 protein or fragment thereof and methods to produce such antibodies; transgenic plants containing the su1 gene, and methods to produce the transgenic plants.

The invention features a nucleic acid isolate able to hybridize under stringent conditions to the complement of a nucleic acid sequence encoding the SU1 protein, and the protein or polypeptide fragment, e.g., immunogenic fragment, thereof encoded by the nucleic acid isolate. The invention also features a recombinant expression vector comprising a nucleic acid isolate able to hybridize under stringent conditions to the complement of a sequence encoding the SU1 protein, and cells transformed with the recombinant expression vector, and methods of expressing the SU1 protein or polypeptide fragment encoded within the recombinant expression vector.

Also featured is a method of producing SU1 protein or polypeptide fragment thereof, comprising transforming a host cell with a nucleic acid able to hybridize under stringent conditions to a sequence encoding the SU1 protein having the amino acid sequence shown in FIG. 1 and linked to a nucleic acid sequence under the control of an inducible promotor, and inducing the inducible promotor to form a fusion protein comprising the SU1 protein.

The invention also features methods of producing antibodies to an SU1 fusion protein, and antibodies produced by such method. Also featured are transgenic plants containing the SU1 gene, and methods of making the transgenic plants.

As used herein, the term "mutate" and "mutation" refers to a nucleic acid sequence that possess one or more base pair insertions, deletions, or changes. As used herein, the term "identify" is intended to include other activities that require identification of an entity, such as isolation or purification. The terms "isolated" or "purified" refer to a nucleic acid or protein sequence that has been separated or isolated from the environment in which it was prepared or in which it naturally occurs. Such nucleic acid or protein sequences may be in the form of chimeric hybrids or fusions, useful for combining the function of the nucleic acid or protein sequences of the invention with other species and also include recombinant forms. The term "determinant" as used herein includes the site on an antigen at which a given antibody molecule binds. The term "immunogenic fragement" refers to a fragment of SU1 protein that reacts with antibodies specific for a determinant of SU1.

The SU1 protein can be used as an alternative hydrolase, including bacterial and fungal starch hydrolases and debranching enzymes, that are utilized in industrial starch processing applications. su1 cDNA, or portions thereof, may be utilized as markers for the identification of specific corn varieties, and for the development of corn varieties with starch properties tailored for specific industrial applications. su1 cDNA can be used to produce these proteins or peptide fragments; to identify nucleic acid molecules encoding related proteins or polypeptides (e.g., homologous polypeptides from related species and heterologous molecules from the same species). Assays for su1 function, production or expression by cells are made possible by the development of antibodies reactive with the SU1 protein.

Other features and advantages of the invention will be apparent from the following description of the preferred embodiments thereof and from the claims.

BRIEF DESCRIPTION OF THE FIGURES

The file of this patent contains at least one color photograph. Copies of this patent with color photograph(s) will be provided by the Patent and Trademark Office upon request and payment of the necessary fee.

FIG. 1 shows the sequence of the su1 cDNA clone SEQ ID no:1 and its amino acid sequence translation SEQ ID no: 2;

FIG. 2 shows the partial sugary1 genomic sequence SEQ ID no:3;

FIG. 3 shows the deduced amino acid sequence of SU1 SEQ ID no:4 and comparison with isoamylase from Pseudomonas SEQ ID no:5;

DETAILED DESCRIPTION OF THE INVENTION

Figure 4C:
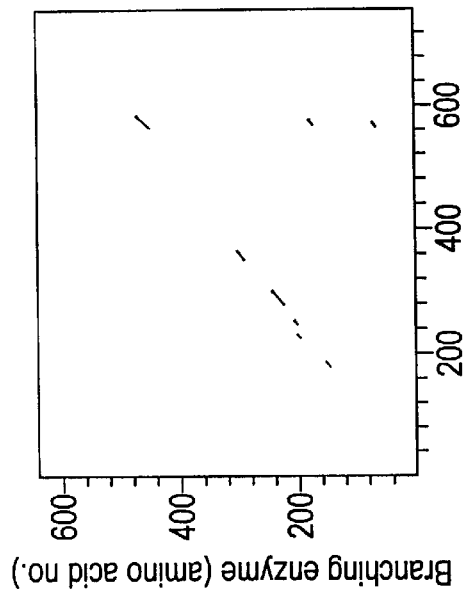
FIG. 4 shows the deduced amino acid sequence of SU1 compared to that of isoamylase from *P. amyloderamosa*, branching enzyme from *Bacillus stearothermophilus*, and α-amylase from *Bacillus megaterium*.

The genes coding for debranching enzymes have not previously been identified or cloned in plants. Currently, bacterial and fungal starch hydrolases, including debranching enzymes, are utilized in industrial applications. A debranching enzyme native to maize would have utility in industrial starch processing applications, and may have unique advantages over the microbial enzymes of the prior art. In addition, portions of the su1 clone may have potential use as markers for the identification of specific corn varieties, and also for the development of corn varieties with starch properties tailored for specific industrial applications.

The 2712-bp nucleotide sequence of the su1 cDNA clone is shown in FIG. 1 (SEQ ID NO:1). A sequence of 14 consecutive T residues is located at one end of the clone, identifying the polyadenylation site and the 3' end of the mRNA. A continuous open reading frame (ORF) of 789 codons begins 88 nucleotides from the 5' end of the cDNA clone and terminates 240 nucleotides prior to the poly(A) adenylation site. This ORF corresponds to a polypeptide of 789 amino acids (SEQ ID NO:2).

Comparison of the cDNA and a partial genomic sequence (FIG. 2; SEQ ID NO:3) identifies four exons and introns in the genomic DNA The four exons extend from nucleotide 658 to nucleotide 1107, nucleotide 1352 to nucleotide 1536, nucleotide 1657 to nucleotide 1753, and nucleotide 2076 to nucleotide 2227 (FIG. 2; SEQ ID NO:3) The exon sequences or the full sequence of SEQ ID NO:3 can be used as probes to obtain the full length genomic sequence by methods well known in the art.

Observing hybridization of su1 cDNA probes to multiple genomic DNA fragments indicates that the gene product, SU1, is a member of a gene family in maize. As many as 14 different regions of the genome form heteroduplexes with a specific portion of the su1 cDNA even under high-stringency conditions. Not all probe segments from the su1 cDNA hybridize with high efficiency to multiple regions of the maize genome, suggesting that specific domains of SU1 are conserved in the putative gene family. The single transcript detected by hybridization to su1 cDNA probes in maize kernels 20 days after pollination originates from Su1 itself, and none of the putative su1-related genes is expressed in this tissue.

The su1-related genes appear to code for enzymes present in germinating kernels or other plant tissues that are active in starch utilization. Multiple α-(1→6) hydrolase activities have been characterized in these tissues (Manners and Rowe, 1969; Lee et al., 1971). The su1 cDNA probes that formed heteroduplexes with multiple genomic segments comprise codons 456 to 818 of the discernible ORF. This region of SU1 is similar in amino acid sequence to Pseudomonas isoamylase (27% identity over 338 aligned residues), but not to as great an extent as the other portions of the maize protein.

The su1 gene produces a mRNA transcript of approximately 2.8 kb in kernels. Amino acid sequence comparisons indicate that regions of SU1 are similar in primary structure to specific portions of several types of enzyme known to hydrolyze glucose homopolymers. These include bacterial debranching enzymes such as isoamylases and pullulanases, enzymes that hydrolyze α-(1→4) glycosidic linkages such as α-amylases and cyclomaltodextrinase, and both prokaryotic and eucaryotic branching enzymes.

Figure 3A:
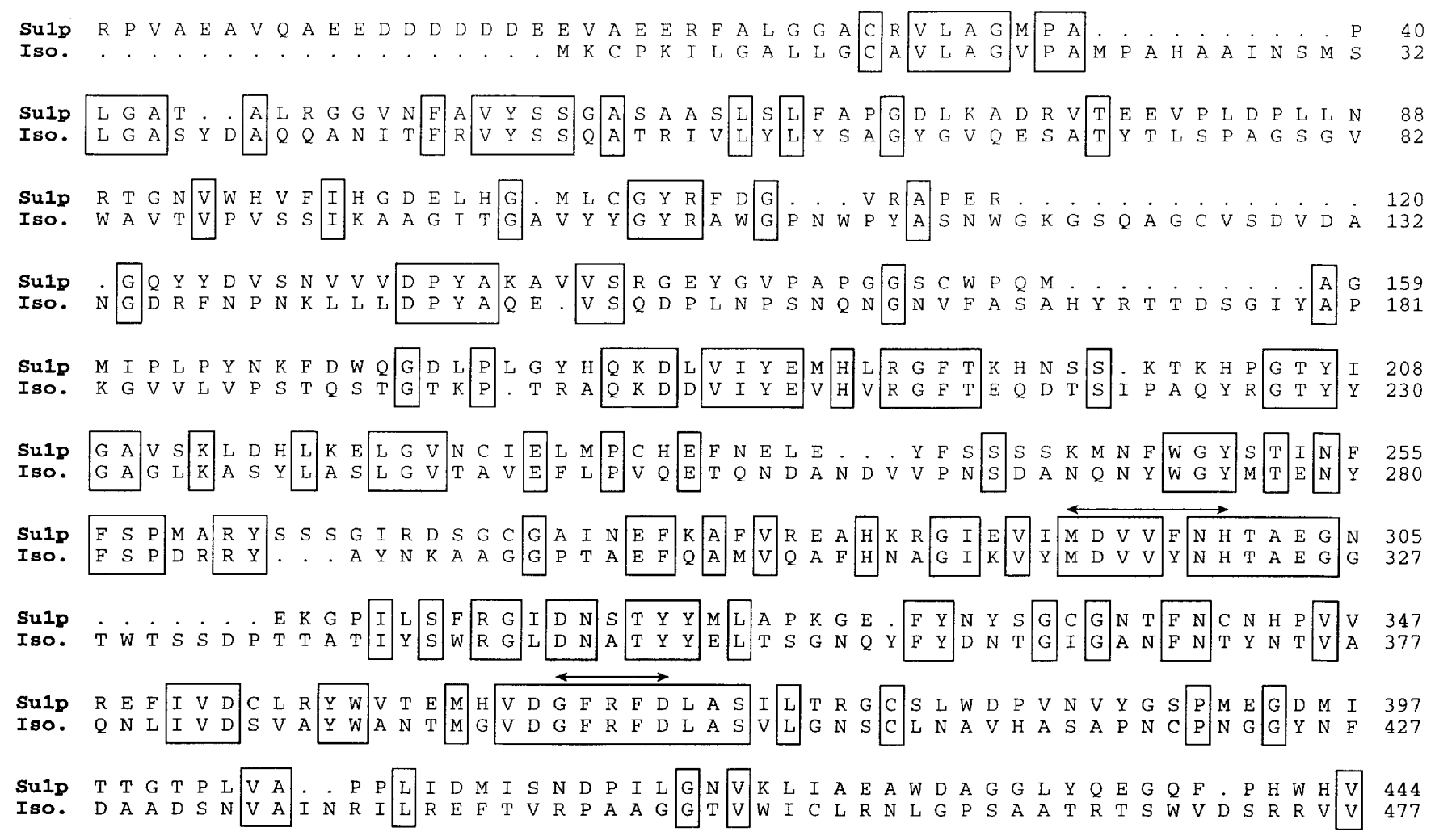
Figure 3B:
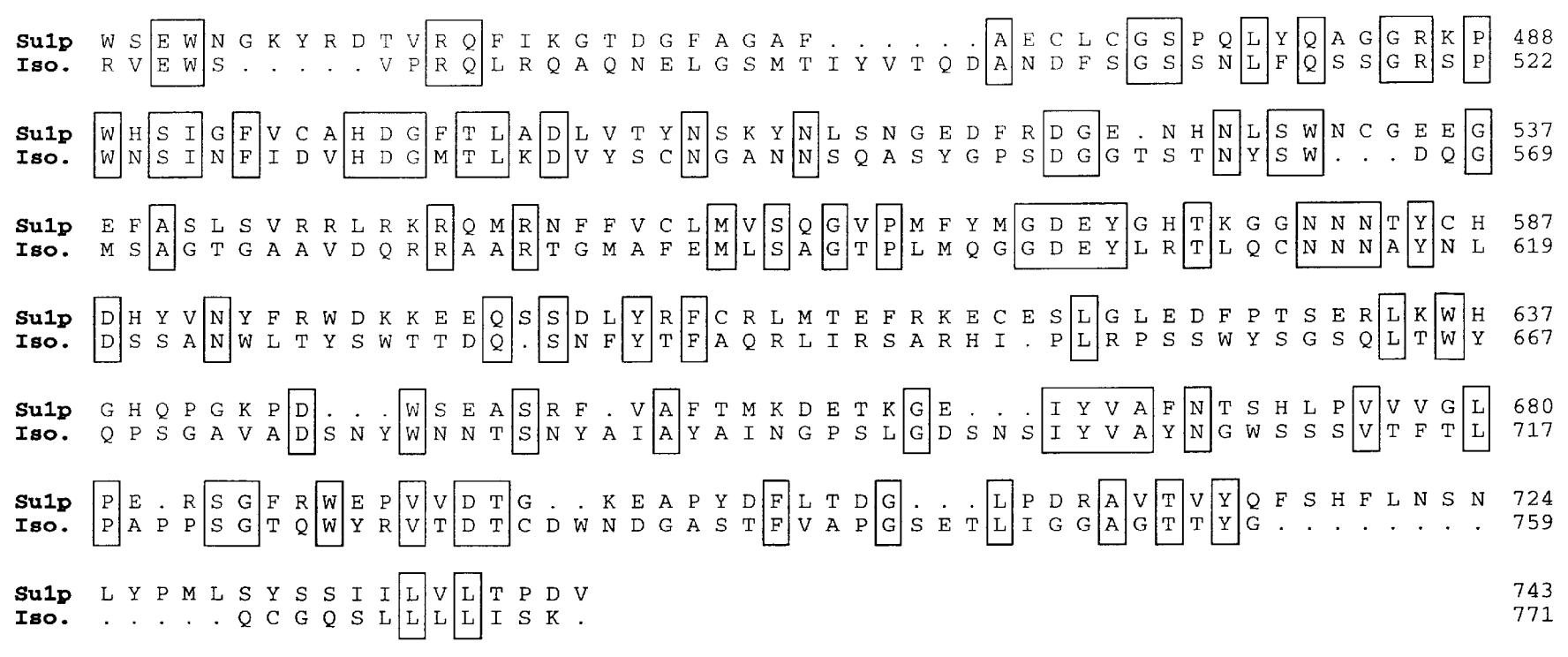

FIG. 3 shows the deduced amino acid sequence of SU1 (SEQ ID NO:4) aligned with that of isoamylase from *P. amyloderamosa* (SEQ ID NO:5). Of the 695 aligned residues, 32% are identical in the two polypeptides. Localized regions show an even higher degree of amino acid sequence identity. For example, of the 99 amino acids between positions 277 and 375 of SU1, 53% are identical to the residue found at that position in isoamylase. Other highly conserved regions of SU1 are residues 476 to 505, where 57% of the 30 amino acids are identical to those of isoamylase, and residues 180 to 222, where 53% of the 43 aligned amino are the same as in the bacterial protein. Two conserved sequence blocks observed previously in all known α-amylases, branching enzymes, and debranching enzymes (Svensson, 1988; MacGregor and Svensson, 1989; Jesperson et al., 1993) are found within SU1. Two additional conserved sequences found specifically in the α-amylases, however, are lacking in SU1.

Amino acid sequence similarity with isoamylase from *P. amyloderamosa* indicates that SU1 is a member of the α-amylase superfamily of starch hydrolytic enzymes. This family includes enzymes from bacteria, fungi, plants, and mammals (Svensson, 1988; MacGregor and Svensson, 1989). The sequence similarity between members of this superfamily is located primarily in two spatially conserved regions that are proposed to form catalytic and starch binding structures within the proteins (Matsuura et al., 1984; Nakajima et al., 1986; Jesperson et al., 1993). SU1 contains both of these conserved regions, and in addition displays extensive primary sequence similarity with the debranching enzymes of the α-amylase superfamily. The characterized enzyme to which SU1 exhibits the highest degree of amino acid sequence identity, isoamylase from Pseudomonas, is known to completely hydrolyze the α-(1→6) linkages of amylopectin and glycogen (Yokobayashi et al., 1970; Amemura et al., 1988). Thus, the nucleotide sequence data indicate that SU1 is a starch debranching enzyme active in maize endosperm.

Figure 4A:
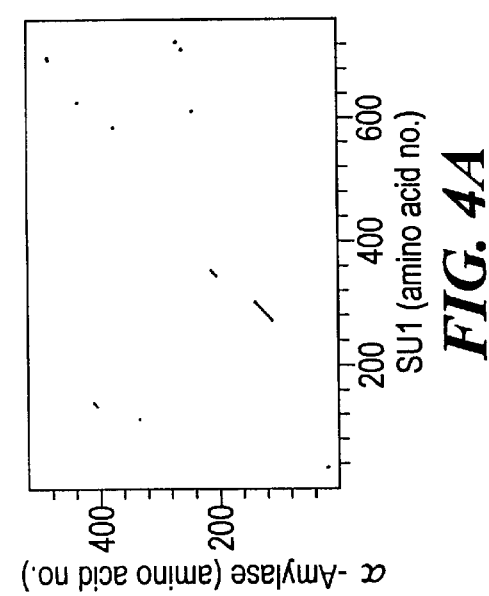
Figure 4B:
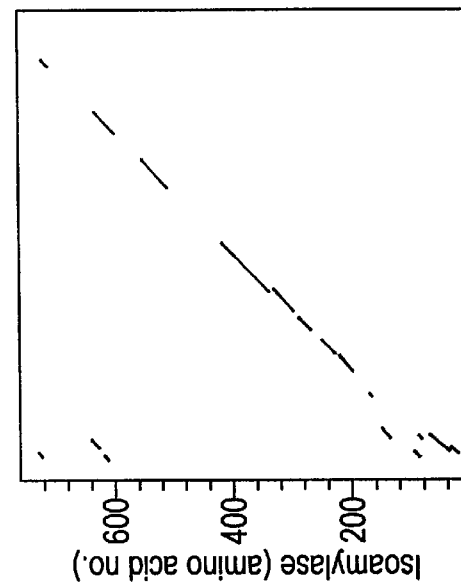

FIG. 4 illustrates the deduced amino acid sequence of SU1 compared to that of isoamylase from *P. amyloderamosa* (GenBank accession number P10342), branching enzyme from *Bacillus stearothermophilus* (GenBank accession number P30538), or α-amylase from *Bacillus megaterium* (GenBank accession number P20845), all from prokaryotic organisms. The sequence identity between SU1 and Pseudomonas isoamylase extends over almost the entire 742 known residues of the maize protein, whereas only short regions of sequence identity are observed between SU1 and the branching enzyme or α-amylase. Thus, among known starch hydrolytic enzymes, SU1 is most closely related to those that hydrolyze α-(1→6) linkages. Among these, the relationship of SU1 to isoamylase is greater than to pullulanase, although the similarity with pullulanase is significantly more extensive than that with branching enzyme or α-amylase. The most extensive amino acid sequence similarity detected is with the deduced product of the *Escherichia coli* gene glgX, a gene of unknown function located in the operon that also codes for a glycogen branching enzyme (Romeo et al., 1988).

The following examples are presented to illustrate the advantages of the present invention and to assist one of ordinary skill in making and using the same. These examples are not intended in any way to otherwise limit the scope of the disclosure.

EXAMPLE I

Isolation and Characterization of SU1 cDNA Clones

The su1 gene locus can be isolated by transposon tagging methodology. Transposon tagging strategy is based on the assumption that insertion of a transposable element in a target gene will cause a mutation that can be identified by a specific phenotype. Two lines of evidence indicated that the cloned transposon-containing genomic DNA is within the su1 locus. First, plants containing any of four independent su1 mutations (su1-R4582::Mu1, su1-R2412, su1-R7110, and su1-R3162) displayed restriction fragment length polymorphisms (RFLP) in the same genomic interval, and these polymorphisms cosegregated with the sugary phenotype. The probability is very low that each of these rare genomic rearrangements would occur coincident with a su1 mutation but not be causally related to su1 function. Second, insertion of Mu1 within the cloned region occurred de novo within the same narrow developmental window in which su1-R4582::Mu1 arose.

Figure 5:
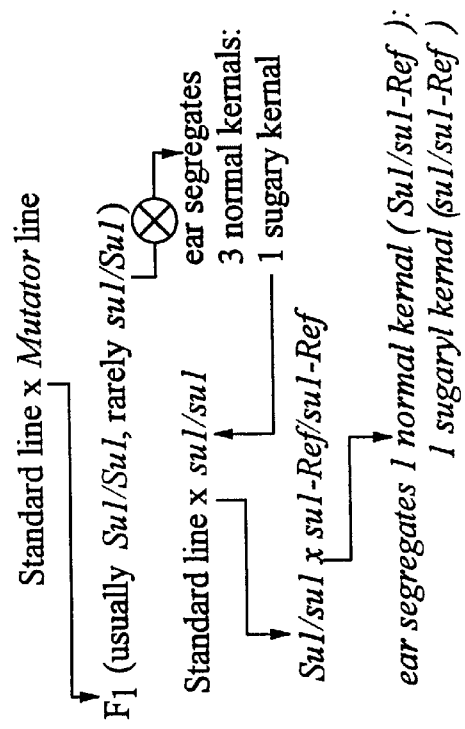
FIG. 5 shows the crossing strategy used in the invention.

The Mutator (Mu) transposable element system can be used to generate new mutations at the su1 gene locus (Scanlon et al., 1994). Referring now to FIG. 5, mutations at the su1 gene locus are generated by crossing active Mutator plants with standard lines homozygous for the non-mutant allele Su1. The F1 progeny are grown and self-pollinated, and the resulting F2 ears are examined for 3:1 segregation of normal and sugary kernels. Sugary kernels from individual F2 ears are planted, and the resultant plants are crossed to standard lines. Progeny from this cross (heterozygous for the putative su1 mutation) are planted and crossed to tester plants homozygous for su1-Ref. Allelism of the new mutation with su1-Ref is indicated by 1:1 segregation of normal-:sugary kernels on the resulting ears.

Figure 6A:
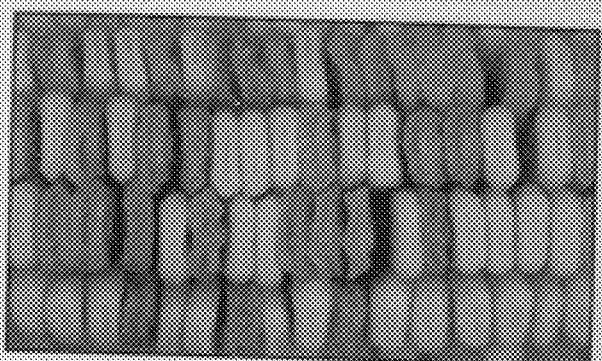
FIG. 6A shows an ear of corn resulting from the cross of FIG. 5.

FIG. 6A shows a typical ear resulting from this cross, which contained sugary and normal kernels at approximately equal frequencies. These data indicate the new mutation did not complement su1-Ref, and thus most likely is allelic to mutations at the su1 gene locus. The one-to-one segregation ratio also confirmed that the sugary phenotype of the original mutant kernel is a single gene trait. Five new su1 mutations are identified in this way and are designated su1-R4582::Mu1, su1-R2412, su1-R7110, su1-R3162, and su1-R8064.

Figure 6B:
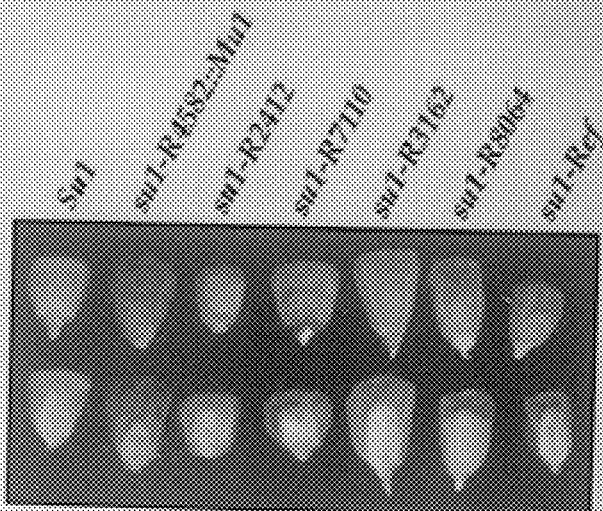
FIG. 6B shows kernel phenotypes in which the su1 gene is present.

FIG. 6B shows the kernel phenotypes that result from each new su1 mutation in the homozygous condition. The mutations su1-R3162 and su1-R8064 resulted in kernel phenotypes similar to that resulting from su1-Ref. The mutation su1-R2412 resulted in a less severe phenotype, with only a slight glassiness and wrinkling at the crown of the kernel. Kernels homozygous for su1-R4582::Mu1 or su1-R7110 generally appeared to be more severely shrunken than su1-Ref homozygotes. These su1 mutations together with su1-Ref can be introgressed into a common inbred line to eliminate potential phenotypic variability resulting from genetic background effects.

Figure 7:
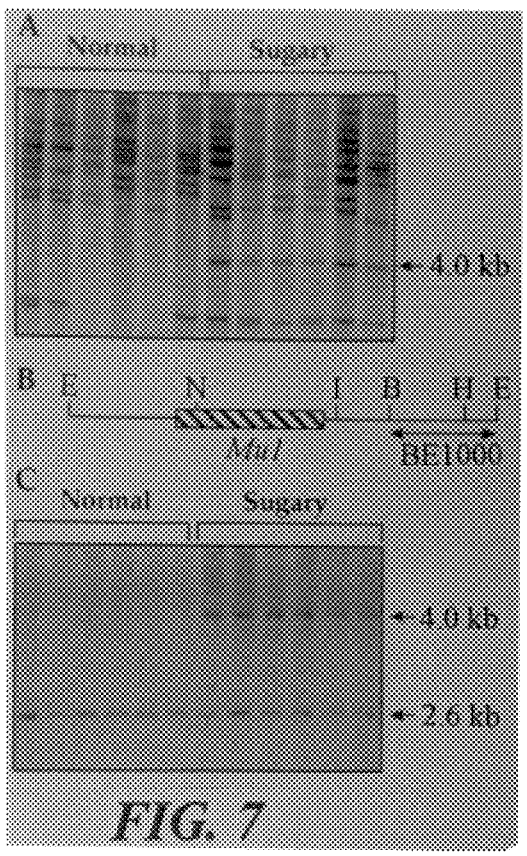
FIG. 7A shows part of a DNA gel blot analysis of DNAs isolated from maize seedlings.
FIG. 7B shows a physical map of the cloned fragment.
FIG. 7C shows a DNA gel blot analysis in which probe BE1000 is hybridized with genomic DNAs from seedlings in the population segregating for su1-R4582::Mu1 and Su1.

Plants containing su1-R4582::Mu1 and others lacking this allele are examined for the presence of a specific Mu transposon that cosegregated with the putative Mu-induced mutation. This analysis utilized the segregating population of sugary kernels (su1-R4582::Mu1/su1-Ref) and sibling normal kernels containing the non-mutant allele Su1 (Su1/su1-Ref) indicated in FIG. 5. FIG. 7A shows part of a DNA gel blot analysis of DNAs isolated from maize seedlings. Genomic DNA from the resulting seedlings is digested with EcoRI and probed on DNA gel blots with the internal 960-bp MluI fragment of Mu1. The length of the fragment marked with the arrow is estimated based on the mobility in the same agarose gel of standards of known nucleotide sequence. These data identified a 4.0-kb EcoRI restriction fragment containing sequences homologous to the transposon Mu1 that cosegregated with su1-R4582::Mu1. In total, the genomic DNAs of seedlings grown from 60 sugary kernels and 57 normal kernels are examined. This specific Mu1-homologous sequence, therefore, either is located within the su1 gene locus or is tightly linked to that locus.

A 4.0-kb EcoRI restriction fragment containing Mu1 can be isolated from the genome of a su1-R4582::Mu1/su1-Ref plant. The fragment initially was identified in a library of size-selected genomic DNA fragments constructed in a bacteriophage λ vector, based on hybridization to a probe internal to Mu1. This recombinant phage is single-plaque purified, and the genomic DNA insert is subcloned as part of plasmid pMJ60. FIG. 7B shows a physical map of the cloned fragment. Restriction sites are indicated for EcoRI (E), NotI (N), HincII (I), HindIII (H), and BamHI (B). The position of restriction enzyme recognition sequences in pMJ60 indicated the transposon present is Mu1 and predicted the position and orientation of this 1.4-kb element within the 4.0-kb EcoRI fragment. The nucleotide sequence of both termini of the transposon matches the known sequence of Mu1 (Barker et al., 1984). A direct repeat sequence of 9 bp is observed in the genomic DNA immediately adjacent to the transposon at each of its termini, typical of Mu transposable elements. In this instance the particular repeated sequence is 5'-CGCGCTCCG-3'.

The region of DNA adjacent to the cloned Mu1 transposon cosegregates with su1-R4582::Mu1, confirming that this sequence is derived from a genomic interval located within or nearby the su1 gene locus. The 1.0-kb BamHI-EcoRI genomic fragment flanking Mu1 in the cloned DNA can be purified and used as a hybridization probe (termed BE1000). FIG. 7C shows sample results of a DNA gel blot analysis in which probe BE1000 is hybridized with genomic DNAs from seedlings in the population segregating for su1-R4582::Mu1 and Su1. The lengths of the fragments marked with arrows are estimated based on the mobility in the same agarose gel of standards of known nucleotide sequence. This genomic probe detected a 4.0-kb EcoRI fragment that is present in all su1-R4582::Mu1/su1-Ref plants, but is missing from all Su1/su1-Ref plants. Thus, the cloned Mu transposon is the same element that is within or tightly linked to the su1 gene locus. Probe BE1000 identifies a second EcoRI fragment of 2.6 kb that is present in all plants examined, and presumably is representative of the non-mutant progenitor allele. This is the only fragment observed in the Su1/su1-Ref plants, indicating the reference mutation is not associated with a discernible deletion or insertion.

Figure 8:
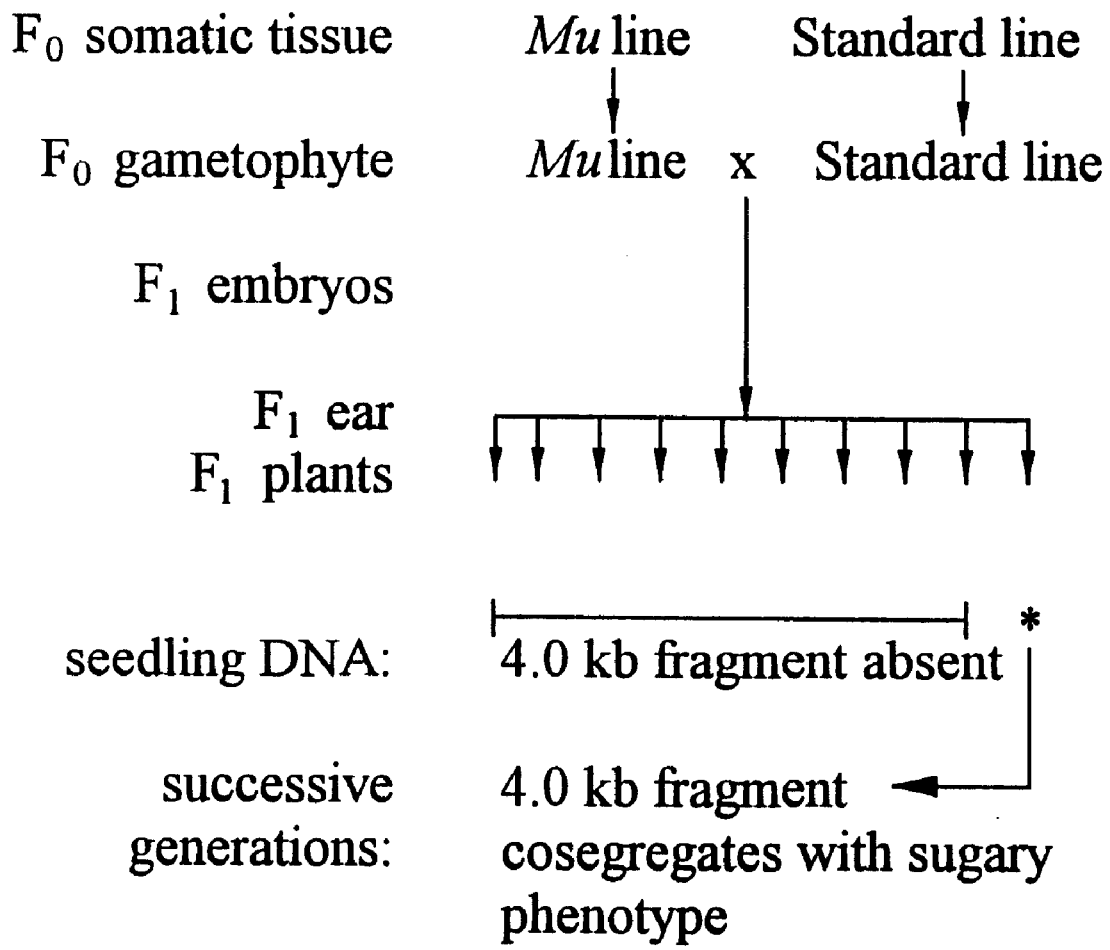
FIG. 8 shows a pedigree analysis of the generations that resulted in the mutation su1-R4582::Mu1.

FIG. 8 illustrates a pedigree analysis of the generations that resulted in the mutation su1-R4582::Mu1. A single F1 plant, indicated with an asterisk, produced sugary kernels on its self-pollinated ear. The self-pollinated ears of 69 additional F1 plants are completely wild type with respect to the sugary phenotype. Genomic DNA was isolated from nine other F1 plant seedlings and examined for the presence of a 4.0-kb EcoRI fragment homologous to genomic probe BE1000. As indicated, none of the F1 seedling DNAs contained a 4.0-kb EcoRI fragment homologous to probe BE1000.

The pedigree shown in FIG. 8 indicates that the cloned DNA is in fact from the su1-R4582::Mu1allele, as opposed to the alternative possibility that the isolated transposon is linked to the su1 gene locus but is not the causative agent of the mutation. This conclusion is based on the observation that the 4.0-kb EcoRI fragment containing Mu1 arose in the same narrow developmental window as did the su1-R4582::Mu1mutation. F1 plants derived from 70 kernels of the F1 ear produced by crossing the F0 Mutator line to an F0 standard line are self-pollinated in the original screen for sugary mutants. Only one of these F1 plants produced sugary kernels on its self-pollinated ear. The su1-R4582::Mu1mutation, therefore, could not have been present in the somatic cells of either F0 parent but must have arisen during gametogenesis in one parent or early in development of the specific F1 embryo that eventually resulted in the sugary kernels. Consistent with this hypothesis, self-pollination of the Mutator F0 parent yielded an ear without sugary kernels. To determine whether the 4.0-kb, Mu1-containing fragment is present in the F0 progenitor plants, nine more kernels from the F1 ear are planted, and genomic DNA can be extracted from the resulting seedlings. In DNA gel blot analysis using probe BE1000 only the 2.6-kb EcoRI fragment is detected. If the 4.0-kb fragment existed in one of the F0 plants, then by Mendelian segregation the fragment would have been present in approximately one-half of the plants analyzed. Thus, the 4.0-kb, Mu1-containing fragment is not present prior to the generation in which su1-R4582::Mu1is formed.

Mutations of the su1 gene locus other than su1-R4582::Mu1can be analyzed to determine whether they also cosegregate with physical alterations in the cloned region of the genome. Populations segregating for the non-mutant allele Su1 and either su1-R2412, su1-R7110, or su1-R3162 can be established as shown in FIG. 5. For each allele genomic DNA from eight su1/su1-Ref plants and eight Su1/su1-Ref plants is digested with EcoRI and probed in DNA gel blot analysis with genomic fragment BE1000.

Figure 9:
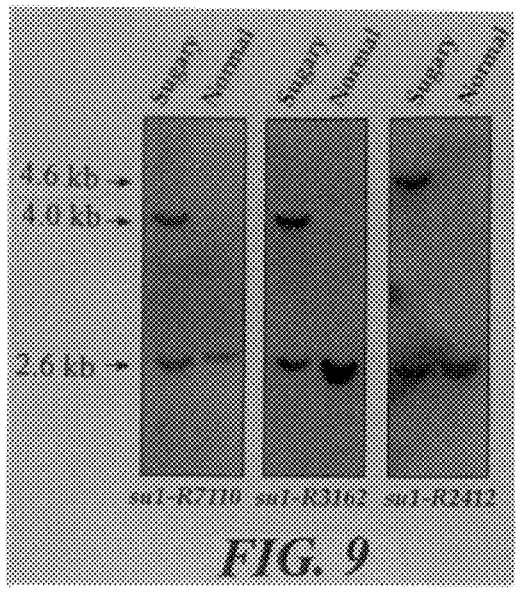
FIG. 9 shows a gel blot of seedling DNA digested with EcoRI and probed with a hybridization probe.

FIG. 9 illustrates that genomic insertions are linked to su1-R2412, su1-R7110, and su1-R3162. Normal and sugary sibling kernels from populations segregating for the non-mutant allele Su1 and either su1-R7110, su1-R3162, or su1-R2412 are germinated as shown in FIG. 5. Genomic DNA from the resulting seedlings is digested with EcoRI and probed on DNA gel blots with fragment BE1000 from the su1-R4582::Mu1genomic clone. The lengths of the fragments marked with arrows are estimated based on the mobility in the same agarose gel of standards of known nucleotide sequence.

As illustrated in FIG. 9, the 4.0-kb EcoRI fragment that in the su1-R7110 and su1-R3162 families is present in all the seedlings grown from sugary kernels but is not observed in any seedlings grown from non-mutant sibling kernels. A different EcoRI fragment, 4.6 kb in length, is found to cosegregate with su1-R2412. As observed previously a 2.6-kb EcoRI fragment is detected by the probe in all plants examined. Because su1-R7110 and su1-R3162 arose in a Mu background, each resulted from the insertion of a 1.4-kb transposon, most likely Mu1, into the same 2.6-kb genomic interval that also is modified in plants containing su1-R4582::Mu1. The mutation su1-R2412 is likely to have occurred via an insertion of a 2.0-kb element into this same region. The broad band of approximately 2.6 kb observed in the su1-R2412 and su1-R3162 populations is resolved in other gels into two fragments of about 2.6 and 2.7 kb. Thus in these backgrounds the non-mutant allele Su1 associates with an EcoRI fragment of 2.7 kb, in contrast to the 2.6-kb fragment observed for this allele in the families segregating for su1-R4582::Mu1or su1-R7110.

Figure 10:
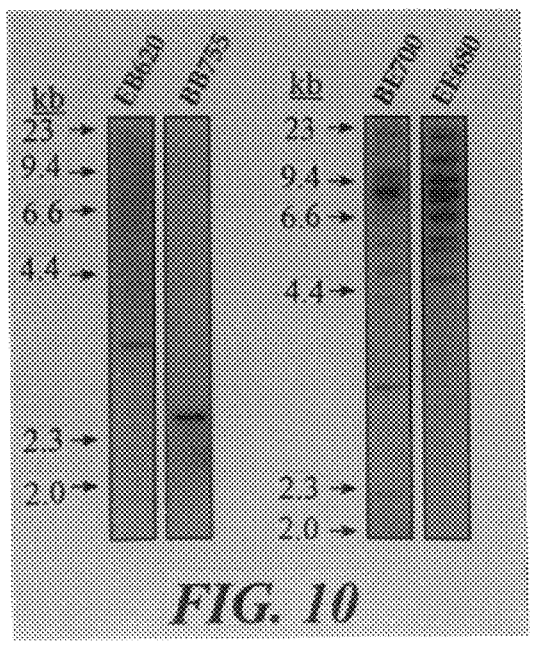
FIG. 10 shows DNA gel blot analysis using various segments of the su1 cDNA as probes.

Referring now to FIG. 10, DNA gel blot analysis using various segments of the su1 cDNA as probes is utilized to examine whether su1 is a unique sequence within the maize genome. In FIG. 10, restriction fragments from the su1 cDNA are used as probes. Maize genomic DNA is digested with BamHI and hybridized with the probes in DNA gel blots under high-stringency conditions. Arrows indicate the mobility in the same agarose gels of standards of known nucleotide sequence.

As illustrated in FIG. 10, a single BamHI fragment hybridizes strongly with cDNA probe EB620 or BB755. In contrast, probe EE680, located downstream of probe BB755, hybridizes with approximately equal efficiency with 14 different BamHI fragments. At most, two of these fragments could be explained by allelic diversity at the su1 gene locus. Twelve other fragments, therefore, contain sequences that are sufficiently complementary in nucleotide sequence to probe EE680 to form heteroduplexes even under the high-stringency conditions used. Probe BE700, located immediately upstream of probe EE680 also detects multiple fragments in the genome. These DNA gel blot data are in agreement with the single hybridization signal obtained using genomic probe BE1000, because all the exons in this genomic interval are contained within cDNA probe BB755.

EXAMPLE II su1 Transcription and Analysis of a su1 cDNA Clone

To characterize the product of the su1 gene locus, SU1, a cDNA clone of the su1 mRNA is obtained. The genomic fragment BE1000 is used as a probe in RNA gel blot analysis and detected a transcript of approximately 2.8 kb in total RNA isolated from wild-type kernels harvested 20 days after pollination. This transcript is more abundant in the polyadenylated RNA fraction than in total RNA, suggesting BE1000 detected the su1 mRNA. A cDNA library constructed from maize endosperm mRNA in a bacteriophage λ vector is screened for hybridization with probe BE1000. In one embodiment, eight hybridizing clones are identified among approximately 200,000 recombinant phage examined. The longest cDNA insert in any of these clones is approximately 2.4-kb. After single plaque purification, the longest cDNA insert is excised from the recombinant bacteriophage and subcloned in phagemid vectors. An additional 280 bp at the 5' end of the cDNA are cloned by polymerase chain reaction (PCR) amplification of the 5' end of the su1 mRNA. Thus the total length of the su1 cDNA clone is approximately 2.7 kb, which, depending on the length of the poly(A) tail, comprises either the complete or nearly complete mRNA sequence.

Figure 11:
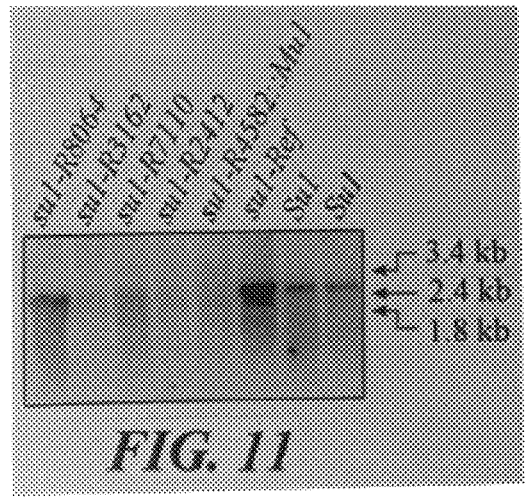
FIG. 11 shows detection of su1 mRNA.

Transcription of the su1 gene locus is examined in normal kernels and sugary kernels homozygous for various su1 mutations, using as a probe a portion of the su1 cDNA. FIG. 11 illustrates detection of su1 mRNA. Total RNA isolated 20 days after pollination from kernels homozygous for the indicated mutation (10 mg per sample) is separated by electrophoresis and probed with fragment EE1780 from the su1 cDNA. The Su1/Su1 kernels are from two different standard lines, F1 hybrid B77/B79 (right-most lane) and F1 hybrid Q66/Q67 (second lane from the right). Arrows indicate the mobility in the same agarose gel of standards of known nucleotide sequence.

As shown in FIG. 11, that in RNA gel blot analysis the cDNA probe EE1780 detected a 2.8 kb mRNA in normal kernels harvested 20 days after pollination. The transcription pattern is identical to that detected by hybridization with the genomic probe BE1000. The 2.8-kb transcript is missing or severely reduced in concentration in kernels homozygous for su1-R4582::Mu1, su1-R2412, su1-R7110, or su1-R3162, whereas transcripts of about this length are present in kernels homozygous su1-R8064 or su1-Ref at seemingly normal levels.

EXAMPLE III

Preparation of Fusion Proteins

The glutathione S-transferase (GST) gene fusion system (Pharmacia Biotech) can be used for the expression and purification of portions of the protein (SU1) coded for by the maize gene sugary1 (su1). The pGEX plasmids designed for this system enable inducible, high-level intracellular expression of genes or gene fragments as fusions with *Schistosoma japonicum* GST. These vectors carry a multiple cloning region to facilitate fusion of a gene fragment to the C-terminus of GST, a tac promoter inducible by the gratuitous lactose analog IPTG, and an internal lac Iq gene for use in any *E. coli* host. Because GST binds reversibly and with high affinity to glutathione, purification of a fusion protein can be accomplished by incubation with a glutathione-affinity matrix such as glutathione-agarose.

Two fragments of the su1 cDNA are used to create fusion proteins. The first construct, termed pAR1, comprises an internal 1.8 kb region of the su1 cDNA that when used as a probe in Southern gel blot analyses recognized multiple regions of maize genomic DNA. The second construct, termed pAR2, comprises a smaller 0.6 kb region of the same su1 fragment used in pAR1. This smaller fragment represents a unique region of maize genomic DNA. The vector pGEX-4T-3 (4.97 kb) is chosen for each construct because it contained an EcoRI site in the multiple cloning region that would enable the su1 cDNA to be transcribed in the proper frame.

A 1782 bp EcoRI fragment from the su1 cDNA subclone pMJ67 (nt 289-nt 2071) is used to make pAR1. This fragment is cloned into the unique EcoRI site of vector pGEX-4T-3 to construct the 6.8 kb pAR1 plasmid. The fusion protein expressed by pAR1, designated GST-SU1-T1, is predicted to contain 594 amino acids of SU1 and to have a size of 93 kD, including the 27.5 kD GST protein. pAR2 is created by deleting all but 595 bp from the 5' end of the su1 EcoRI fragment (nt 289-nt 864) that is used for the construction of pAR1. For this construct, the su1 region downstream of nt 864 is removed by digestion of pAR1 with HindIII (at nt 864 in the su1 cDNA) and SaII (a site within the multiple cloning region of the vector). Following removal of this fragment, the remaining portion of pAR1 which contained the vector and 595 bp of su1 cDNA is purified, treated with the Klenow fragment of DNA polymerase to produce blunt ends, and self-ligated to produce pAR2 (5.6 kb). The fusion protein from pAR2, designated GST-SU1-T2, is predicted to contain 192 amino acids from SU1 and to have a size of 49 kD, including the 27.5 kD GST.

Recombinant plasmids pAR1 and pAR2 are grown in the *E. coli* host strain TG-1. For large scale preparation, a host colony containing either plasmid pAR1 or pAR2 is grown at 30° C. overnight in 100 ml 2XYT media containing 25 ug/ml ampicillin. This culture is used to inoculate 1 liter of the same medium, which is grown at 30° C. until the cells reached an $OD_{600}$ of approximately 1.0. Expression of the fusion protein is then induced by the addition of isopropylthiogalactoside (IPTG) to a concentration of 0.1 mM and incubation at 30° C. for 2 hr. Proteins are harvested from crude bacterial lysates generated by enzymatic digestion with lysozyme. Fusion proteins GST-SU1-T1 and GST-SU1-T2 are purified by passage of the cell lysate over glutathione-agarose affinity columns. Proteins are analyzed by sodium dodecylsulfate polyacrylamide gel electrophoresis (SDS-PAGE) followed by staining with Coomassie blue, and by immunoblot analysis using an ECL chemiluminescent system (Amersham) with anti-GST antibody (Molecular Probes, Inc.) as the primary antibody and anti-rabbit IgG horseradish peroxidase conjugate (BioRad Laboratories) as the secondary antibody. Both GST-SU1-T1 and GST-SU1-T2 are detected by these means and each is of the predicted size.

In an alternative embodiment, su1 protein (SU1) can be expressed in *E. coli* using the pET Expression System (Novagen). This system utilizes the bacteriophage T7 promoter to drive expression of a recombinant protein and offers the means for efficient detection and purification of the protein. Expression of full-length or near full-length SU1 enables an in vitro analysis of the biochemical function of the protein, specifically its ability to hydrolyze branched polysaccharides.

Two constructs have been designed to express the recombinant SU1 protein. The first contains the near full-length cDNA, beginning at nt 289 of the su1 cDNA (an EcoRI site in the adaptor of the lambda cDNA clone) and terminating at nt 2616 (an XhoI site). The second contains the full-length cDNA, beginning at nt 86 (an NcoI site that contains the putative translation start signal) and terminating at nt 2616 (XhoI site). The XhoI site is in the 3' region of the cDNA past the translational stop codons. The vector pET-29b(+) is chosen for both constructs because the su1 cDNA is transcribed in the correct reading frame when either EcoRI or NcoI is used as a cloning site. This vector contains the bacteriophage T7 promoter and terminator sequences, and a lac operator sequence. To aid in detection and purification, pET-29b(+) contains both a His-Tag sequence and an S-Tag sequence. The His-Tag sequence allows the recombinant protein to be purified by metal chelation chromatography, and the S-Tag sequence allows the protein to be affinity-purified with ribonuclease S-protein and quantified with a homogeneous assay.

Fusion proteins produced with the above assays are cleaved using a protease, such as thrombin, and the products purified by chromatography. The pET-29b(+) vector contains a thrombin cleavage site that can be used to remove the upstream S-Tag by digestion with the site-specific protease thrombin.

Cloning of either the 2327 bp EcoRI/XhoI region or the 2530 bp NcoI/XhoI region of the su1 cDNA into pET-29b(+) requires some initial subcloning manipulations which are within the skills of the ordinary skilled practicioner. This is because a portion of the 5' end of the su1 cDNA is obtained by RACE-PCR amplification, and exists as a separate clone. In addition, the su1 cDNA contains an internal EcoRI site (at nt 2061).

The 2327 bp EcoRI/XhoI region can be united and cloned into pET-29b(+) by first digesting pAR1 with KpnI, which cuts at a unique site within the su1 sequence, and XhoI, which cuts at a unique site within the multiple cloning region of the vector, to remove the 1315 bp KpnI-XhoI fragment. pMJ99, which contains a 2.9 kb KpnI insert from the lambda su1 cDNA clone in pUC119, is digested with KpnI and XhoI to release the 1858 bp KpnI/XhoI 3' region of the su1 cDNA. The 1858 bp KpnI-XhoI fragment excised from pMJ99 is ligated to the KpnI-, XhoI-digested pAR1. This last construct, designated pAR3, is partially digested with EcoRI and XhoI to release the 2327 bp EcoRI/XhoI fragment for ligation to EcoRI-, XhoI-digested pET-29b(+). This final clone is designated pAR4.

Cloning of the 2530 bp NcoI/XhoI region of su1 cDNA into pET-29b(+) is achieved by first digesting pMJ125, which contains the su1 5' RACE-PCR product as a 620 bp EcoRI/BamHI fragment in pUC119, with NcoI and Pm1I to release and purify the 425 bp NcoI/Pm1I fragment. The 425 bp fragment is cloned into NcoI-, Pm1I-digested pAR4.

Recombinant su1 protein is tested for the ability to hydrolyze various branched polysaccharides. In one embodiment, enzyme activity is assayed by the release of maltotriose from pullulan, an ordered glucopolysaccharide, with dinitrosalicylic acid reagent according to the method of Bernfeld (1951). Assays to measure the release of glucose from dextrin and the release of various reducing sugars from amylopectin and/or glycogen following incubation of the enzyme with these substrates can also be employed.

EXAMPLE IV

Preparation and Analysis of Polyclonal Antibodies

New Zealand White rabbits are inoculated with fusion protein GST-SU1-T1 or GST-SU1-T2. Fusion proteins are purified from *E. coli* lysates by affinity chromatography with glutathione-agarose. An initial intramuscular injection of 300 µg protein emulsified in Freund's complete adjuvant is followed by two to three booster injections with 200 µg protein emulsified in Freund's incomplete adjuvant. Sera from sample test bleeds harvested after one week each boost is tested for SU1 specificity by immunoblot analysis The sera is used as primary antibody to detect purified GST-SU1-T1 and GST-SU1-T2 proteins as well as total proteins extracted from maize endosperms harvested 20 days after pollination (DAP). This is a tissue and time period when the su1 gene is known to be transcribed, according to Northern gel blot analysis. Preliminary immunoblot results obtained using serum collected following the third boost of one rabbit inoculated with fusion protein GST-SU1-T2 identifies a protein of approximately 80 kD among total proteins isolated from wild type maize endosperm tissue 20 DAP. This protein is not detected in proteins harvested from su1 mutant endosperms 20 DAP.

EXAMPLE V

Preparation of Monoclonal Antibodies

Monoclonal antibodies reactive with SU1 can be prepared by according to methods known in the art (e.g., Milstein, Sci. Amer. 243:66-64 (1980); Kohler, Science 233:1281-1286 (1986); Milstein, Science 231:1261-1268 (1986)). Briefly, a mouse can be immunized with SU1 protein or a fragment thereof, and its spleen removed several weeks later. A mixture of lymphocytes and plasma cells from this spleen can be fused in in vitro with myeloma cells by exposing them to polyethylene glycol, a polymer that induces cell fusion. A mutant myeloma cell line lacking hypoxanthine-guanosine phosphoribosyl transferase (HGPRT) can be used to enable hybrids to be easily selected. The cells can be grown in a medium containing hypoxanthine, aminopterin (methotrexate), and thymine (HAT medium) to kill unfused myeloma cells. The hybridoma cells so produced and their progeny indefinitely produce large amounts of the homogeneous antibody specified by the parent cell from the spleen and can be grown in wells in tissure culture plates. Supernatants from these wells can be screened for the presence of antibody molecules specific for the antigen of interest. The cells in positive wells are cloned and screened again to obtain hybridomas of a single type which produce the antibody of interest.

EXAMPLE VI

Development of Transgenic Plants with Modified Expression of su1

Microprojectile bombardment has demonstrated high success for generation of transgenic plants. Microprojectiles coated with a gene that regulates pigmentation have been successfully targeted to a variety of tissues (Ludwig et al., Science 247:449-450 (1990)). Microprojectile bombardment is a useful technique in which to form transgenic maize plants using the gene of the present invention. In one embodiment, microprojectile particles coated with a vector containing the cDNA of the gene coupled with appropriate promoter and termination sequences are inserted into the genome. A genetic marker is included in the vector to detect transformed cells. Using the transformation procedure and the appropriate promotor sequence (e.g., mutated su1 promoter sequences, seed-specific promoters from other genes, or inducible promotor, such as a heat shock promotor), maize plants are generated in which the timing and/or level of expression of the su1 gene locus is modified in endosperm tissue. Use of promoters that specify gene expression in plant tissues other than endosperm can be incorporated to express su1 in tissues in which it is not normally expressed. Also, modifications of the coding region of su1 allow for production of transgenic plants that have mutated sul enzyme activity (e.g., enhanced or reduced binding or catalytic activity) in endosperm.

Experimental Procedures

Maize Stocks, Genetic Crosses, and Allele Nomenclature

Mutations at the sugary1 (su1) gene locus are generated by crossing active Mutator (Mu) plants (Robertson, 1978) with standard lines as shown in FIG. 5. Standard lines are the F1 hybrids B77/B79 or Q66/Q67. These four inbred lines have no history of Mutator activity. Mutant alleles su1-R4582::Mu1, su1-R2412, su1-R7110 and su1-R3162 are identified following the self-pollinations of the F1 plants #82-83-4582-43, #87-2412-24, #79-7110-2, and #83-3162-15, respectively. Allele su1-R8064 is identified following the open pollination of F1 plant #88-8064-1, derived from the cross of a Mutator plant with a plant homozygous for colored aleurone1 shrunken1 bronze1 waxy1. These plant numbers are the laboratory designations used to identify each allele; inclusion of the term "Mu1" indicates the particular mutation is known to have resulted from insertion of a Mu1 transposon. Stock number 413B, from the Maize Genetics Cooperation Stock Center, is used for tests of allelism between each of the five new su1 mutations and the reference allele su1-Ref.

DNA and RNA Gel Blot Analyses

Standard procedures are used for DNA and RNA gel blot analyses (Ausubel et al., 1989; Sambrook et al., 1989). Maize DNA is isolated from seedling tissue by the method of Dellaporta (1983). Approximately 10 mg of genomic DNA is digested with 30 units of restriction enzyme, separated by electrophoresis in 0.8% agarose gels, and transferred to a nylon membrane (Magnacharge, Micron Separations Inc., Westboro, Mass.). Membranes are hybridized to DNA probes at 65° C. in 6X SSC (1X SSC is 0.15 M NaCl, 0.015 M sodium citrate), 1% sarkosyl, 50 mg/mL denatured salmon sperm DNA (Sigma Chemical Co., St. Louis, Mo.); the probes are radioactively labeled by the random primer method. The membranes then are washed twice in 2X SSC, 0.1% SDS for 30 min at 65° C., twice in 0.2X SSC, 0.1% SDS for 20 min at 65° C., and once in 5 mM Tris-HCl, pH 8.0, for 5 to 10 min at 65° C., and are exposed to x-ray film for 1 to 4 days.

Total RNA is isolated as described (Cone et al., 1986) from maize kernels harvested 20 days after pollination and stored at −80° C. During this procedure water-soluble polysaccharide is removed from the nucleic acid fractions prepared from su1 mutant kernels by centrifugation at 100,000×g for 1 hr in a Beckman model TL-100 centrifuge. Under these conditions the water-soluble polysaccharide is separated as a gelatinous pellet from the aqueous phase that contains the RNA. Approximately 5 mg total RNA is denatured and separated by electrophoresis in the presence of formaldehyde and then transferred to nylon membranes (Ausubel et al., 1989). Membranes are hybridized at 42° C. to radioactively labeled DNA probes in 50% formamide, 1 M NaCl, 1% SDS, 10% dextran sulfate, 50 mg/mL denatured salmon sperm DNA. After hybridization the membranes are ished as described above for DNA gel blot analysis. Radioactivity remaining on the membranes is detected using the Phosphorimager (Molecular Dynamics).

Genomic and cDNA Cloning Procedures

Approximately 200 mg of genomic DNA isolated and pooled from three su1-Ref/su1-R4582::Mu1 seedlings is digested with EcoRI and separated by electrophoresis. DNA is eluted and purified from gel fractions containing fragments approximately 3 to 5 kb in length and ligated to the bacteriophage λ vector NM1149 (Scalenghe et al., 1981). The genomic library is used to infect *Escherichia coli* C600hflA cells (Sambrook et al., 1989), and approximately 200,000 plaques are screened with the Mu1-specific probe MM960. Seven hybridizing clones are single-plaque purified and the genomic 4.0-kb EcoRI fragment present in one recombinant λ clone (H-4) is subcloned into the phagemid vector pBluescript KS+ (Stratagene), producing pMJ60.

A portion of the su1 cDNA is isolated as follows. A maize endosperm cDNA library in the bacteriophage vector λgt11 is produced using methods known in the art. EcoRI adapters are ligated to cDNA molecules during preparation of this library. Approximately 200,000 plaques from this library are screened with genomic probe BE1000. DNA from eight different hybridizing clones is digested with EcoRI. The largest cDNA insert present is 2.4 kb in length, and comprised two EcoRI fragments of 1.8 and 0.6 kb. These two fragments are subcloned in pBluescript KS+ to produce pMJ67 and pMJ68, respectively.

Amplification of 5' cDNA

To obtain the 5' end of the su1 cDNA, a modification of the rapid amplification of cDNA ends (RACE) protocol (Frohman et al., 1988) is used. Polyadenylated RNA from maize kernels (2 mg) is reverse transcribed using the sul-specific primer 5'-GTATGTACTATTATCTATCCC-3' (10 pmol) (nucleotides 1191-1171) (SEQ ID NO:6). Unincorporated nucleotides and excess primer is removed using Centricon 100 filters (Amicon, Beverly, Mass.). Poly (A)-tailed cDNA is amplified by polymerase chain reaction (PCR) using the su1-specific primer 5'-GGGATCATACCAGCCATTTGA-3' (25 pmol) (nucleotides 713-693) (SEQ ID NO:7), RACE (dT)17 adapter (10 pmol), and RACE amplification primer (25 pmol) (Frohman et al., 1988). The amplified products are digested with BamHI and EcoRI and cloned in phagemid vector pUC119. The resulting plasmid, pMJ125, is characterized by nucleotide sequence analysis and found to extend beyond the 5' terminus of the cDNA clone present in pMJ67.

Nucleic Acid Hybridization Probes

The 960-bp MluI fragment MM960, contained within Mu1, is excised from plasmid pMJ9 (Barker et al., 1984) and used to detect genomic and cloned copies of this transposon. Probe BE1000, a 1.0-kb BamHI-EcoRI fragment comprising part of the su1 gene locus, is excised from plasmid PMJ60. su1 cDNA probes are the 755-bp BamHI fragment BB755, the 700-bp BamHI-EcoRI fragment BE700, and the 1780-bp EcoRI fragment EE1780 (all excised from plasmid pMJ67), the 680-bp EcoRI fragment EE680 (excised from plasmid pMJ68), and the 620-bp EcoRI-BamHI fragment EB620 (excised from plasmid pMJ125).

Nucleotide Sequence Analysis

Nucleotide sequence is determined by the chain termination method (Sanger et al., 1977) using Sequenase Version 2.0 (U.S. Biochemical Corp.). To determine the sequence of the maize genomic DNA adjacent to the Mu1 termini in su1-R4582::Mu1, two EcoRI-NotI fragments from the insert in pMJ60 are subcloned in phagemid vectors. Each of these two fragments contained one of the Mu1 termini. Sequence is determined using oligonucleotide primers from within each terminus and extending in the 3' direction towards the end of the transposon (5'-GGCTGTCGCGTGCGT-3'(SEQ ID NO:8), and 5'-GCGTACGTCTCTAAA-3' (SEQ ID NO:9)). Portions of pMJ60 and all of pMJ67, pMJ68, and pMJ125 are analyzed using various oligonucleotide primers; the original plasmids and various subclones derived from them are used as templates. To sequence across the EcoRI site internal to the cDNA insert in phage λ clone H-4, the 2.9-kb KpnI fragment from this phage is subcloned in pBluescript KS+ to form pMJ99. This fragment extends from the KpnI site in the cDNA to the KpnI site of λgt11. Of the 2712-bp cDNA sequence, approximately 2300 bp are analyzed on both strands, and all restriction sites used for subcloning are crossed.

The GCG sequence analysis software package (Genetics Computer Group, Madison, Wis.) is used for database searches and amino acid sequence alignments. The GenBank accession number for the su1 cDNA sequence is U18908.

USE

Corn starch is the primary carbohydrate source for producing fuel ethanol, high fructose corn syrup, and other products. Fungal glucoamylases that are currently used in corn starch processing hydrolyze α-(1,6) glucosidic linkages at approximately 1/30th the rate of α-1,4 linkages. The debranching step is the rate limiting step and lengthens the starch refining process up to 75 hours. The use of isolated SU1 as a replacement for the bacterial and fungal enzymes currently used in the starch processing industry will significantly increase the efficiency of corn starch processing and thus reduce both time and cost requirements. In addition, the SU1 protein may be capable of acting on starch derivatives that are convertible to biodegradable products.

Availability of the su1 cDNA facilitates direct examination of the putative maize endosperm debranching enzyme SU1 for the ability to hydrolyze α-(1→6) glycosidic linkages. The substrate specificities of bacterial isoamylases and pullulanases have been characterized (Gunja-Smith et al., 1970; Yokobayashi et al., 1970; Lee and Whelan, 1971; Harada et al., 1972; Kainuma et al., 1978), and this information suggests specific biochemical functions of SU1. Isoamylase is equally active towards amylopectin or glycogen, and the hydrolysis rate of α-(1→6) linkages in the polysaccharides is about 10-fold greater than in small oligosaccharides. Pullulanase is moderately active in the hydrolysis of amylopectin and is unable to hydrolyze glycogen; its preferred substrate is the ordered glucopolysaccharide pullulan. Neither debranching enzyme releases single glucosyl residues from α-(1→6) linkages. Pullulanase will release maltosyl groups, whereas isoamylase only releases maltotriosyl groups and larger oligosaccharides from branched molecules. Another activity specific to isoamylase is the ability to hydrolyze linkages between α-maltosaccharides and a tyrosine residue of the mammalian protein glycogenin, the putative primer for glycogen biosynthesis (Lomako et al., 1992). If this activity is conserved in SU1, then it is possible that the maize debranching enzyme could affect starch biosynthesis in the endosperm by regulating initiation of polysaccharide chain growth.

Although the invention has been shown and described with respect to illustrative embodiments thereof, it should be appreciated that the foregoing and various other changes, omissions and additions in the form and detail thereof may be made without departing from the spirit and scope of the invention as delineated in the claims.

What is claimed is:

1. A nucleic acid isolate that hybridizes under stringent conditions to the complement of a nucleic acid sequence encoding the SU1 protein having the amino acid sequence shown in FIG. 1 (SEQ ID NO:2).

2. The nucleic acid isolate of claim 1, wherein said nucleic acid is DNA.

3. The nucleic acid isolate of claim 2, wherein said nucleic acid comprises the nucleotide sequence shown in FIG. 1 (SEQ ID NO:1).

4. The nucleic acid isolate of claim 2, wherein said nucleic acid comprises the nucleotide sequence shown in FIG. 2 (SEQ ID NO:3).

5. The nucleic acid isolate of claim 1, wherein said nucleic acid is RNA.

6. The nucleic acid isolate of claim 1, wherein said nucleic acid sequence encodes a polypeptide having SU1 biological activity.

7. The nucleic acid isolate of claim 1, wherein said nucleic acid encodes a polypeptide having the amino acid sequence shown in FIG. 1 (SEQ ID NO:2).

8. A nucleic acid isolate of claim 1, wherein said nucleic acid encodes a polypeptide that is recognized by an antibody specific for an SU1 determinant.

9. The nucleic acid isolate of claim 1, comprising nucleic acid encoding an SU1 catalytic binding structure and an SU1 starch binding structure.

10. The nucleic acid isolate of claim 1, including exons extending from nucleotide 658 to nucleotide 1107, nucleotide 1352 to nucleotide 1536, nucleotide 1657 to nucleotide 1753, and nucleotide 2076 to nucleotide 2227 of SEQ ID NO:3.

11. A nucleic acid fragment comprising nucleotides 658 to 1107 of SEQ ID NO:3.

12. A nucleic acid fragment comprising nucleotides 1352 to 1536 of SEQ ID NO:3.

13. A nucleic acid fragment comprising nucleotides 1657 to 1753 of SEQ ID NO:3.

14. A nucleic acid fragment comprising nucleotides 2076 to 2227 of SEQ ID NO:3.

15. A nucleic acid fragment comprising codons 456 to 818 of the nucleic acid sequence of FIG. 1 (SEQ ID NO:1).

16. A recombinant expression vector comprising a nucleic acid isolate that hybridizes under stringent conditions to the complement of a sequence encoding the SU1 protein having the amino acid sequence shown in FIG. 1 (SEQ ID NO:2).

17. A composition comprising a cell transformed with the recombinant expression vector of claim 16.

18. A method of producing an SU1 protein or polypeptide fragment thereof, comprising expressing the recombinant expression vector of claim 16.

19. A method of producing an SU1 protein or polypeptide fragment thereof, comprising the steps of:

transforming a host cell with a nucleic acid that hybridizes under stringent conditions to a sequence encoding the SU1 protein having the amino acid sequence shown in FIG. 1 (SEQ ID NO:2), said sequence encoding the SU1 protein linked to a nucleic acid sequence under the control of an inducible promotor; and inducing said inducible promotor to form a fusion protein comprising the SU1 protein.

20. The method of claim 19, further comprising the steps of recovering said SU1 protein from said fusion protein.

21. The method of claim 19, wherein said fusion protein comprises a protein or polypeptide fragment comprising the amino acid sequence of FIG. 1 (SEQ ID NO:2).

22. A transgenic plant comprising a genome including a foreign DNA sequence encoding the SU1 protein having the amino acid sequence shown in FIG. 1 (SEQ ID NO:2).

23. The transgenic plant of claim 22, wherein said sequence encoding the SU1 protein is under the control of a mutated su1 promotor.

24. The transgenic plant of claim 22, wherein said sequence encoding the SU1 protein is under the control of a seed-specific promotor.

25. The transgenic plant of claim 22, wherein said sequence encoding the SU1 protein is under the control of an inducible promotor.

26. The transgenic plant of claim 22, wherein said sequence encoding SU1 is modified to produce altered SU1 activity.

27. A method of making a transgenic plant comprising the steps of:

providing plant cells comprising a genome without a nucleic acid sequence encoding the SU1 protein;

providing a plurality of microprojectiles;

coating said plurality of microprojectiles with a vector containing a DNA sequence encoding the SU1 protein having the amino acid sequence shown in FIG. 1, said DNA sequence including a promotor sequence, a terminator sequence, and a genetic marker;

bombarding said plant cells with said coated microprojectiles; and detecting said transformed cells by said genetic marker.

* * * * *

SEQUENCE LISTING (1) GENERAL INFORMATION:

(iii) NUMBER OF SEQUENCES: 9

(2) INFORMATION FOR SEQ ID NO:1:

(i) SEQUENCE CHARACTERISTICS:
      (A) LENGTH: 2712 base pairs
      (B) TYPE: nucleic acid
      (C) STRANDEDNESS: single
      (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(ix) FEATURE:
    (A) NAME/KEY: Coding Sequence
    (B) LOCATION: 1...2454
    (D) OTHER INFORMATION:

(xi) SEQUENCE DESCRIPTION: SEQ ID NO:1:

| | | | | | | | | | | | | | | | | |
|---|---|---|---|---|---|---|---|---|---|---|---|---|---|---|---|---|
| CGT | CTC | GTC | ACA | CAC | TCC | ACT | CGA | ACG | CAC | TAC | TTG | ATC | GGC | CAA | AGC | 48 |
| Arg | Leu | Val | Thr | His | Ser | Thr | Arg | Thr | His | Tyr | Leu | Ile | Gly | Gln | Ser | |
| 1 | | | | 5 | | | | | 10 | | | | | 15 | | |
| CAA | ACG | AAC | TGG | GCT | CCC | TCC | CCT | CCA | CTT | CCT | CTC | CCC | ATG | GCG | CAG | 96 |
| Gln | Thr | Asn | Trp | Ala | Pro | Ser | Pro | Pro | Leu | Pro | Leu | Pro | Met | Ala | Gln | |
| | | | 20 | | | | | 25 | | | | | 30 | | | |
| CAG | CTC | CCC | TGC | GTC | TCG | TCG | CCG | CGC | CCG | CTG | CTC | GCC | GTG | CCC | GCG | 144 |
| Gln | Leu | Pro | Cys | Val | Ser | Ser | Pro | Arg | Pro | Leu | Leu | Ala | Val | Pro | Ala | |
| | | 35 | | | | | 40 | | | | | 45 | | | | |
| GGC | CGG | TGG | CGC | GCC | GGC | GTG | CGG | GGC | CGG | CCC | AAT | GTG | GCG | GGA | CTG | 192 |
| Gly | Arg | Trp | Arg | Ala | Gly | Val | Arg | Gly | Arg | Pro | Asn | Val | Ala | Gly | Leu | |
| | 50 | | | | | 55 | | | | | 60 | | | | | |
| GGG | CGG | GGG | CGG | CTG | TCT | CTC | CAC | GCC | GCC | GCC | GCG | CGG | CCC | GTG | GCC | 240 |
| Gly | Arg | Gly | Arg | Leu | Ser | Leu | His | Ala | Ala | Ala | Ala | Arg | Pro | Val | Ala | |
| 65 | | | | | 70 | | | | | 75 | | | | | 80 | |
| GAG | GCG | GTG | CAG | GCG | GAG | GAG | GAC | GAC | GAC | GAC | GAC | GAG | GAG | GTG | | 288 |
| Glu | Ala | Val | Gln | Ala | Glu | Glu | Asp | Asp | Asp | Asp | Asp | Glu | Glu | Val | | |
| | | | | 85 | | | | | 90 | | | | | 95 | | |
| GCC | GAG | GAG | AGG | TTC | GCG | CTG | GGC | GGC | GCG | TGC | CGG | GTG | CTC | GCG | GGA | 336 |
| Ala | Glu | Glu | Arg | Phe | Ala | Leu | Gly | Gly | Ala | Cys | Arg | Val | Leu | Ala | Gly | |
| | | | 100 | | | | | 105 | | | | | 110 | | | |
| ATG | CCC | GCG | CCG | CTC | GGC | GCC | ACC | GCG | CTC | CGC | GGC | GGT | GTC | AAC | TTC | 384 |
| Met | Pro | Ala | Pro | Leu | Gly | Ala | Thr | Ala | Leu | Arg | Gly | Gly | Val | Asn | Phe | |
| | | 115 | | | | | 120 | | | | | 125 | | | | |
| GCC | GTC | TAC | TCC | AGC | GGT | GCC | TCC | GCC | GCG | TCG | CTG | AGC | CTC | TTC | GCT | 432 |
| Ala | Val | Tyr | Ser | Ser | Gly | Ala | Ser | Ala | Ala | Ser | Leu | Ser | Leu | Phe | Ala | |
| | 130 | | | | | 135 | | | | | 140 | | | | | |
| CCC | GGC | GAC | CTC | AAG | GCG | GAT | AGG | GTG | ACC | GAG | GAG | GTG | CCC | CTC | GAT | 480 |
| Pro | Gly | Asp | Leu | Lys | Ala | Asp | Arg | Val | Thr | Glu | Glu | Val | Pro | Leu | Asp | |
| 145 | | | | 150 | | | | | 155 | | | | | 160 | | |
| CCC | CTG | CTC | AAC | CGA | ACG | GGA | AAC | GTG | TGG | CAC | GTG | TTC | ATC | CAC | GGG | 528 |
| Pro | Leu | Leu | Asn | Arg | Thr | Gly | Asn | Val | Trp | His | Val | Phe | Ile | His | Gly | |
| | | | 165 | | | | | 170 | | | | | 175 | | | |
| GAC | GAG | CTG | CAC | GGC | ATG | CTC | TGC | GGA | TAC | AGG | TTC | GAT | GGC | GTG | TTC | 576 |
| Asp | Glu | Leu | His | Gly | Met | Leu | Cys | Gly | Tyr | Arg | Phe | Asp | Gly | Val | Phe | |
| | | 180 | | | | | 185 | | | | | 190 | | | | |
| GCC | CCT | GAG | CGC | GGA | CAG | TAC | TAC | GAT | GTG | TCC | AAC | GTT | GTG | GTG | GAT | 624 |
| Ala | Pro | Glu | Arg | Gly | Gln | Tyr | Tyr | Asp | Val | Ser | Asn | Val | Val | Val | Asp | |
| | 195 | | | | | 200 | | | | | 205 | | | | | |
| CCA | TAC | GCT | AAG | GCA | GTG | GTA | AGC | CGA | GGT | GAA | TAT | GGT | GTG | CCT | GCG | 672 |
| Pro | Tyr | Ala | Lys | Ala | Val | Val | Ser | Arg | Gly | Glu | Tyr | Gly | Val | Pro | Ala | |
| 210 | | | | | 215 | | | | | 220 | | | | | | |
| CCT | GGT | GGT | AGT | TGT | TGG | CCT | CAA | ATG | GCT | GGT | ATG | ATC | CCT | CTT | CCC | 720 |
| Pro | Gly | Gly | Ser | Cys | Trp | Pro | Gln | Met | Ala | Gly | Met | Ile | Pro | Leu | Pro | |
| 225 | | | | 230 | | | | | 235 | | | | | 240 | | |
| TAT | AAT | AAG | TTT | GAT | TGG | CAA | GGT | GAC | CTA | CCC | CTT | GGG | TAC | CAT | CAG | 768 |
| Tyr | Asn | Lys | Phe | Asp | Trp | Gln | Gly | Asp | Leu | Pro | Leu | Gly | Tyr | His | Gln | |
| | | | 245 | | | | | 250 | | | | | 255 | | | |
| AAG | GAC | CTT | GTC | ATA | TAT | GAA | ATG | CAT | TTG | CGT | GGA | TTC | ACA | AAG | CAC | 816 |
| Lys | Asp | Leu | Val | Ile | Tyr | Glu | Met | His | Leu | Arg | Gly | Phe | Thr | Lys | His | |
| | | 260 | | | | | 265 | | | | | 270 | | | | |
| AAC | TCA | AGC | AAG | ACA | AAA | CAC | CCA | GGA | ACT | TAC | ATT | GGT | GCT | GTG | TCA | 864 |
| Asn | Ser | Ser | Lys | Thr | Lys | His | Pro | Gly | Thr | Tyr | Ile | Gly | Ala | Val | Ser | |
| | 275 | | | | | 280 | | | | | 285 | | | | | |

-continued

| | | |
|---|---|---|
| AAG CTT GAC CAT CTA AAG GAA CTT GGA GTG AAC TGT ATA GAG CTA ATG<br>Lys Leu Asp His Leu Lys Glu Leu Gly Val Asn Cys Ile Glu Leu Met<br>290                  295                  300 | 912 |
| CCC TGC CAT GAG TTC AAT GAG CTA GAG TAC TTC AGC TCC TCT TCG AAG<br>Pro Cys His Glu Phe Asn Glu Leu Glu Tyr Phe Ser Ser Ser Ser Lys<br>305                  310                  315                  320 | 960 |
| ATG AAC TTC TGG GGA TAT TCC ACA ATA AAT TTT TTC TCA CCA ATG GCA<br>Met Asn Phe Trp Gly Tyr Ser Thr Ile Asn Phe Phe Ser Pro Met Ala<br>                  325                  330                  335 | 1008 |
| AGA TAT TCT TCA AGT GGC ATA AGA GAC TCT GGA TGT GGT GCC ATA AAT<br>Arg Tyr Ser Ser Ser Gly Ile Arg Asp Ser Gly Cys Gly Ala Ile Asn<br>                340                  345                  350 | 1056 |
| GAA TTT AAA GCT TTT GTA AGG GAG GCC CAC AAA CGG GGA ATT GAG GTG<br>Glu Phe Lys Ala Phe Val Arg Glu Ala His Lys Arg Gly Ile Glu Val<br>            355                  360                  365 | 1104 |
| ATC ATG GAT GTT GTC TTC AAT CAT ACA GCT GAA GGT AAT GAG AAA GGC<br>Ile Met Asp Val Val Phe Asn His Thr Ala Glu Gly Asn Glu Lys Gly<br>370                  375                  380 | 1152 |
| CCA ATA TTA TCC TTT AGG GGG ATA GAT AAT AGT ACA TAC TAC ATG CTT<br>Pro Ile Leu Ser Phe Arg Gly Ile Asp Asn Ser Thr Tyr Tyr Met Leu<br>385                  390                  395                  400 | 1200 |
| GCA CCT AAG GGA GAG TTT TAT AAT TAT TCT GGT TGT GGA AAT ACC TTC<br>Ala Pro Lys Gly Glu Phe Tyr Asn Tyr Ser Gly Cys Gly Asn Thr Phe<br>                  405                  410                  415 | 1248 |
| AAT TGT AAT CAT CCT GTA GTC CGT GAA TTT ATA GTG GAT TGC TTG AGA<br>Asn Cys Asn His Pro Val Val Arg Glu Phe Ile Val Asp Cys Leu Arg<br>                420                  425                  430 | 1296 |
| TAC TGG GTA ACA GAA ATG CAT GTT GAT GGT TTT CGT TTT GAC CTT GCA<br>Tyr Trp Val Thr Glu Met His Val Asp Gly Phe Arg Phe Asp Leu Ala<br>            435                  440                  445 | 1344 |
| TCT ATA CTG ACC AGA GGA TGC AGT CTA TGG GAT CCA GTT AAT GTG TAT<br>Ser Ile Leu Thr Arg Gly Cys Ser Leu Trp Asp Pro Val Asn Val Tyr<br>450                  455                  460 | 1392 |
| GGA AGT CCA ATG GAA GGT GAC ATG ATT ACG ACA GGG ACA CCT CTT GTT<br>Gly Ser Pro Met Glu Gly Asp Met Ile Thr Thr Gly Thr Pro Leu Val<br>465                  470                  475                  480 | 1440 |
| GCC CCA CCA CTT ATT GAC ATG ATT AGC AAT GAC CCA ATT CTT GGA AAT<br>Ala Pro Pro Leu Ile Asp Met Ile Ser Asn Asp Pro Ile Leu Gly Asn<br>                  485                  490                  495 | 1488 |
| GTC AAG CTC ATT GCT GAA GCA TGG GAT GCA GGA GGT CTC TAT CAA GAA<br>Val Lys Leu Ile Ala Glu Ala Trp Asp Ala Gly Gly Leu Tyr Gln Glu<br>                500                  505                  510 | 1536 |
| GGT CAG TTT CCT CAC TGG AAC GTT TGG TCA GAG TGG AAT GGA AAG TAT<br>Gly Gln Phe Pro His Trp Asn Val Trp Ser Glu Trp Asn Gly Lys Tyr<br>            515                  520                  525 | 1584 |
| CGC GAT ACC GTG CGT CAG TTC ATC AAA GGC ACA GAT GGA TTT GCT GGT<br>Arg Asp Thr Val Arg Gln Phe Ile Lys Gly Thr Asp Gly Phe Ala Gly<br>530                  535                  540 | 1632 |
| GCT TTT GCT GAA TGC CTA TGT GGA AGT CCA CAG TTA TAC CAG GCA GGG<br>Ala Phe Ala Glu Cys Leu Cys Gly Ser Pro Gln Leu Tyr Gln Ala Gly<br>545                  550                  555                  560 | 1680 |
| GGG AGG AAG CCT TGG CAC AGT ATC GGC TTT GTA TGT GCA CAC GAT GGA<br>Gly Arg Lys Pro Trp His Ser Ile Gly Phe Val Cys Ala His Asp Gly<br>                  565                  570                  575 | 1728 |
| TTT ACA CTG GCT GAT TTG GTC ACA TAC AAT AGC AAG TAC AAC TTG TCA<br>Phe Thr Leu Ala Asp Leu Val Thr Tyr Asn Ser Lys Tyr Asn Leu Ser<br>                580                  585                  590 | 1776 |
| AAT GGT GAG GAC TTC AGA GAT GGG GAA AAT CAT AAT CTT AGC TGG AAT<br>Asn Gly Glu Asp Phe Arg Asp Gly Glu Asn His Asn Leu Ser Trp Asn<br>                595                  600                  605 | 1824 |

```
TGT GGG GAG GAA GGA GAA TTT GCA AGT CTG TCA GTC CGA AGA TTA AGG        1872
Cys Gly Glu Glu Gly Glu Phe Ala Ser Leu Ser Val Arg Arg Leu Arg
        610                 615                 620

AAG AGG CAA ATG CGC AAT TTC TTT GTT TGT CTT ATG GTT TCT CAG GGA        1920
Lys Arg Gln Met Arg Asn Phe Phe Val Cys Leu Met Val Ser Gln Gly
625                 630                 635                 640

GTT CCA ATG TTC TAC ATG GGC GAT GAA TAT GGT CAC ACA AAG GGA GGG        1968
Val Pro Met Phe Tyr Met Gly Asp Glu Tyr Gly His Thr Lys Gly Gly
                645                 650                 655

AAC AAC AAT ACG TAC TGC CAT GAC CAT TAT GTC AAT TAT TTC CGT TGG        2016
Asn Asn Asn Thr Tyr Cys His Asp His Tyr Val Asn Tyr Phe Arg Trp
            660                 665                 670

GAT AAG AAG GAA GAA CAA TCC TCT GAT TTG TAC AGA TTC TGC CGT CTC        2064
Asp Lys Lys Glu Glu Gln Ser Ser Asp Leu Tyr Arg Phe Cys Arg Leu
        675                 680                 685

ATG ACC GAA TTC CGC AAA GAA TGT GAA TCT CTT GGC CTT GAG GAC TTC        2112
Met Thr Glu Phe Arg Lys Glu Cys Glu Ser Leu Gly Leu Glu Asp Phe
    690                 695                 700

CCG ACT TCA GAA CGG TTG AAA TGG CAC GGT CAT CAG CCC GGG AAG CCT        2160
Pro Thr Ser Glu Arg Leu Lys Trp His Gly His Gln Pro Gly Lys Pro
705                 710                 715                 720

GAC TGG TCA GAG GCA AGC CGA TTC GTT GCC TTC ACC ATG AAG GAC GAA        2208
Asp Trp Ser Glu Ala Ser Arg Phe Val Ala Phe Thr Met Lys Asp Glu
                725                 730                 735

ACC AAA GGC GAG ATC TAC GTG GCC TTC AAC ACC AGT CAC CTT CCG GTG        2256
Thr Lys Gly Glu Ile Tyr Val Ala Phe Asn Thr Ser His Leu Pro Val
            740                 745                 750

GTT GTT GGG CTT CCA GAG CGC TCT GGG TTC CGA TGG GAG CCG GTG GTG        2304
Val Val Gly Leu Pro Glu Arg Ser Gly Phe Arg Trp Glu Pro Val Val
        755                 760                 765

GAC ACC GGC AAG GAG GCA CCA TAT GAC TTC CTC ACC GAT GGC CTG CCA        2352
Asp Thr Gly Lys Glu Ala Pro Tyr Asp Phe Leu Thr Asp Gly Leu Pro
    770                 775                 780

GAT CGT GCT GTC ACC GTC TAC CAG TTC TCT CAT TTC CTC AAC TCC AAT        2400
Asp Arg Ala Val Thr Val Tyr Gln Phe Ser His Phe Leu Asn Ser Asn
785                 790                 795                 800

CTC TAT CCT ATG CTC AGC TAC TCC TCC ATC ATC CTT GTA TTG CGC CCT        2448
Leu Tyr Pro Met Leu Ser Tyr Ser Ser Ile Ile Leu Val Leu Arg Pro
                805                 810                 815

GAT GTC TGAAAGAAGC AGATACAATA GAGTATACTA TAGCGGTTGT TCTCTAGGCT GTA     2507
Asp Val

GCATGCAGTG GAAACTGGAA AATGTTGGGG TTGCTCTGTT GTCGGTAGTT TACATGCGCA      2567

TGTCGGTATG TGTACATAAA GCTGGTGGAT CTCAGTTCTC AGATCGGACT CGAGACGGCA      2627

AAACCATTGC CAGTTGGCTG GTTCTCTGAA GTTTTGTTTG GTGTAAAGAA ATGGTGGTCC      2687

ATCATCTACT CTTTTTTTTT TTTTT                                            2712

(2) INFORMATION FOR SEQ ID NO:2:

(i) SEQUENCE CHARACTERISTICS:
        (A) LENGTH: 818 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (v) FRAGMENT TYPE: internal
```

(vi) ORIGINAL SOURCE:

(xi) SEQUENCE DESCRIPTION: SEQ ID NO:2:

```
Arg Leu Val Thr His Ser Thr Arg Thr His Tyr Leu Ile Gly Gln Ser
 1               5                  10                  15

Gln Thr Asn Trp Ala Pro Ser Pro Pro Leu Pro Leu Pro Met Ala Gln
             20                  25                  30

Gln Leu Pro Cys Val Ser Ser Pro Arg Pro Leu Leu Ala Val Pro Ala
         35                  40                  45

Gly Arg Trp Arg Ala Gly Val Arg Gly Arg Pro Asn Val Ala Gly Leu
     50                  55                  60

Gly Arg Gly Arg Leu Ser Leu His Ala Ala Ala Arg Pro Val Ala
 65                  70                  75                  80

Glu Ala Val Gln Ala Glu Glu Asp Asp Asp Asp Glu Glu Val
                 85                  90                  95

Ala Glu Glu Arg Phe Ala Leu Gly Gly Ala Cys Arg Val Leu Ala Gly
                100                 105                 110

Met Pro Ala Pro Leu Gly Ala Thr Ala Leu Arg Gly Gly Val Asn Phe
            115                 120                 125

Ala Val Tyr Ser Ser Gly Ala Ser Ala Ser Leu Ser Leu Phe Ala
        130                 135                 140

Pro Gly Asp Leu Lys Ala Asp Arg Val Thr Glu Val Pro Leu Asp
145                 150                 155                 160

Pro Leu Leu Asn Arg Thr Gly Asn Val Trp His Val Phe Ile His Gly
                165                 170                 175

Asp Glu Leu His Gly Met Leu Cys Gly Tyr Arg Phe Asp Gly Val Phe
            180                 185                 190

Ala Pro Glu Arg Gly Gln Tyr Tyr Asp Val Ser Asn Val Val Val Asp
        195                 200                 205

Pro Tyr Ala Lys Ala Val Val Ser Arg Gly Glu Tyr Gly Val Pro Ala
    210                 215                 220

Pro Gly Gly Ser Cys Trp Pro Gln Met Ala Gly Met Ile Pro Leu Pro
225                 230                 235                 240

Tyr Asn Lys Phe Asp Trp Gln Gly Asp Leu Pro Leu Gly Tyr His Gln
                245                 250                 255

Lys Asp Leu Val Ile Tyr Glu Met His Leu Arg Gly Phe Thr Lys His
            260                 265                 270

Asn Ser Ser Lys Thr Lys His Pro Gly Thr Tyr Ile Gly Ala Val Ser
        275                 280                 285

Lys Leu Asp His Leu Lys Glu Leu Gly Val Asn Cys Ile Glu Leu Met
    290                 295                 300

Pro Cys His Glu Phe Asn Glu Leu Glu Tyr Phe Ser Ser Ser Lys
305                 310                 315                 320

Met Asn Phe Trp Gly Tyr Ser Thr Ile Asn Phe Ser Pro Met Ala
                325                 330                 335

Arg Tyr Ser Ser Ser Gly Ile Arg Asp Ser Gly Cys Gly Ala Ile Asn
            340                 345                 350

Glu Phe Lys Ala Phe Val Arg Glu Ala His Lys Arg Gly Ile Glu Val
        355                 360                 365

Ile Met Asp Val Val Phe Asn His Thr Ala Glu Gly Asn Glu Lys Gly
    370                 375                 380

Pro Ile Leu Ser Phe Arg Gly Ile Asp Asn Ser Thr Tyr Tyr Met Leu
385                 390                 395                 400

Ala Pro Lys Gly Glu Phe Tyr Asn Tyr Ser Gly Cys Gly Asn Thr Phe
```

-continued

```
                  405                 410                 415
Asn Cys Asn His Pro Val Val Arg Glu Phe Ile Val Asp Cys Leu Arg
            420                 425                 430
Tyr Trp Val Thr Glu Met His Val Asp Gly Phe Arg Phe Asp Leu Ala
            435                 440                 445
Ser Ile Leu Thr Arg Gly Cys Ser Leu Trp Asp Pro Val Asn Val Tyr
            450                 455                 460
Gly Ser Pro Met Glu Gly Asp Met Ile Thr Thr Gly Thr Pro Leu Val
465                 470                 475                 480
Ala Pro Pro Leu Ile Asp Met Ile Ser Asn Asp Pro Ile Leu Gly Asn
            485                 490                 495
Val Lys Leu Ile Ala Glu Ala Trp Asp Ala Gly Gly Leu Tyr Gln Glu
            500                 505                 510
Gly Gln Phe Pro His Trp Asn Val Trp Ser Glu Trp Asn Gly Lys Tyr
            515                 520                 525
Arg Asp Thr Val Arg Gln Phe Ile Lys Gly Thr Asp Gly Phe Ala Gly
            530                 535                 540
Ala Phe Ala Glu Cys Leu Cys Gly Ser Pro Gln Leu Tyr Gln Ala Gly
545                 550                 555                 560
Gly Arg Lys Pro Trp His Ser Ile Gly Phe Val Cys Ala His Asp Gly
            565                 570                 575
Phe Thr Leu Ala Asp Leu Val Thr Tyr Asn Ser Lys Tyr Asn Leu Ser
            580                 585                 590
Asn Gly Glu Asp Phe Arg Asp Gly Glu Asn His Asn Leu Ser Trp Asn
            595                 600                 605
Cys Gly Glu Gly Glu Phe Ala Ser Leu Ser Val Arg Arg Leu Arg
610                 615                 620
Lys Arg Gln Met Arg Asn Phe Val Cys Leu Met Val Ser Gln Gly
625                 630                 635                 640
Val Pro Met Phe Tyr Met Gly Asp Glu Tyr Gly His Thr Lys Gly Gly
            645                 650                 655
Asn Asn Asn Thr Tyr Cys His Asp His Tyr Val Asn Tyr Phe Arg Trp
            660                 665                 670
Asp Lys Lys Glu Glu Gln Ser Ser Asp Leu Tyr Arg Phe Cys Arg Leu
            675                 680                 685
Met Thr Glu Phe Arg Lys Glu Cys Glu Ser Leu Gly Leu Glu Asp Phe
690                 695                 700
Pro Thr Ser Glu Arg Leu Lys Trp His Gly Gln Pro Gly Lys Pro
705                 710                 715                 720
Asp Trp Ser Glu Ala Ser Arg Phe Val Ala Phe Thr Met Lys Asp Glu
            725                 730                 735
Thr Lys Gly Glu Ile Tyr Val Ala Phe Asn Thr Ser His Leu Pro Val
            740                 745                 750
Val Val Gly Leu Pro Glu Arg Ser Gly Phe Arg Trp Glu Pro Val Val
            755                 760                 765
Asp Thr Gly Lys Glu Ala Pro Tyr Asp Phe Leu Thr Asp Gly Leu Pro
            770                 775                 780
Asp Arg Ala Val Thr Val Tyr Gln Phe Ser His Phe Leu Asn Ser Asn
785                 790                 795                 800
Leu Tyr Pro Met Leu Ser Tyr Ser Ser Ile Ile Leu Val Leu Arg Pro
            805                 810                 815
Asp Val
```

(2) INFORMATION FOR SEQ ID NO:3:

(i) SEQUENCE CHARACTERISTICS:
        (A) LENGTH: 2523 base pairs
        (B) TYPE: nucleic acid
        (C) STRANDEDNESS: double
        (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:3:

```
GAATTCTCTT TTGAGTTAAT TAACCACCCA CACCGTACAA ATTGAGCAAG CCTTTGTTAT      60
CTCCACATAC ATGTATATTA ATATAAGATA CATATATCTC GTTTTTTAAA GAAATATCGC     120
ATTGGGTTTA TTATTATTTT AAGACTAGTT TGTAAACTCT ATTTTTCTGA GAAATTCCTA     180
TTTTTCAAGA GAAAATAAAC TAATTTATTT GAAAAAATGT AAAACTTTTG ATAAAATAGG     240
ATTGTCAAAC TAGACCTTAT TATATGTATA TGTATATGTA TAAAGTATCA CTGTGAAAAG     300
TATGAAAAAA GTTTAGTTCT TTTCTTTTGG TGAATATAAG AGTATAAATA ATAAAAAGTG     360
GAATAGTATA GTGCCTGAAA AGCGGCAACT AGATCGTGTT TGCCAGTACG CGGGCCCCAC     420
AGAAAAAGCC CACGTCCGCC TCCCGCTGCG AAAAAACGAC ACGGGCCGAG TGGACGACGG     480
TGGCCGGACG CAGACGCAGA CGCTTCCGGC TGTGAAAAAA CGCACGCTCC GACCCCGCCG     540
TCCGCCGATC CGAGGCTCCG GCCCCACTCT GTCAGCGTCA CTGCGTGAGC GAGCGGGCGG     600
TGTGCGTGAT CCGGACCCGC CCCTCCTCAC ACCGTCGCGC ACGGGAGCCA AGACGACGCC     660
GCGCTCCGTC GCATCCACCT CGTCTCGTCA CACACTCCAC TCGAACGCAC TACTTGATCG     720
GCCAAAGCCA AACGAACTGG GCTCCCTCCC CTCCACTTCC TCTCCCCATG GCGCAGAAGC     780
TCCCCTGCGT CTCGTCGCCG CGCCCGCTGC TCGCCGTGCC CGCGGGCCGG TGGCGCGCCG     840
GCGTGCGGGG CCGGCCCAAT GTGGCGGGAC TGGGGCGGGG GCGGTTGTCT CTCCACGCCG     900
CCGCCGCGCG GCCCGTGGCC GAGGCGGTGC AGGCGGAGGA GGACGACGAC GACGACGACG     960
AGGAGGTGGC CGAGGAGAGG TTCGCGCTGG GCGGCGCGTG CCGGGTGCTC GCGGGAATGC    1020
CCGCGCCGCT CGGCGCCACC GCGCTCCGCG GCGGTGTCAA CTTCGCCGTC TACTCCAGCG    1080
CCCACCCCTA GTCTTTGATG AATGCAATTT CTGCAACCGG TGCTCGGATC CTTCTGTGTC    1140
GTTCTTCTTC TCTTTTGGAA TTTGAATGGA AGGGAAGTCG GCTTACTAAC TTACTCCTCT    1200
ATTTCTCTCT CTCTCGAATA ACTTGCTTCT CGATGCTGTA CGCTAATTGT TGGCTTCATA    1260
CGATACGCCG GTGCTGAAAT GGACTGAGTT CTCTGTATTC CTGGTATGAT GCAGGATAGG    1320
GTGACGCAGG AGGTGCCCCT CGATCCCCTG CTCAACCGAA CGGGAAACGA GAGGCACGTG    1380
TTCATCCACG GGACCAGCT GCACGGCATG CTCTACGGAT ACAGGTTCGA TGCGTGTTCG    1440
CCCCTGAGCG CGGACAGTAC TACGATGTGT CCAACGTTGT GGTGGATCCA TACGCTAAGG    1500
TGACGGGCTG TTGTCTTTAC TTTGGCTATG CGTGTGAGCT GTGACACACT CAGAAACTGA    1560
TTGCTGGGTG CTTGCTCATG TTTTAGTTGT TTACTTCTTC TTGTTGTTGT TTTCTCTAGG    1620
CAGGCAGTGG TAAGCCGAGG TGAATATGGT GTGCCTGCGC CTGGTGGTAG TTGTTGGCCT    1680
CAAATGGCTG GTATGATCCC TCTTCCCTAT AATAAGGTAA GCCAGAACTA CTCTCGCTCA    1740
CACTACCTTC CTGTTTGCTT TCATGCTGTA TCCTTCTCTT CCAGTTTTAT GATCTCCCCA    1800
```

```
TGTCTGACTC ACTCACGATT AAACAATAAA AAGAAACCAC CGCATATATT TGGCTCATTG    1860

ATGCATTTGA AAAGCTCCGC ATGAACTAAC TGAACAAAGC GCCTAGAACT ATCAACTGTA    1920

GGTTAGGACT CATTGGCTTC TGCTTACTTA GTTTCTGCCT TTGCCAGGTT CAAATGGAGT    1980

CGAAGTTATA TTTCACGTGC CTATTATGTT GTCCTGTATG ATAAGGTTGC ATTTGCAGTT    2040

TGATTGGCAA GGTGACCTAC CCTTGGGTAC CATCAGAAGG ACCTTGTCAT ATATGAAATG    2100

CATTTGCGTG GATTCACAAA GCACAACTCA AGCAAGACAA AACACCCAGG AACTTACATT    2160

GGTGCTGTGT CAAAGCTTGA CCATCTAAAG GTACTGTTAC GAACAGACTA GCTATAAGTC    2220

TGCGAAAGTG TCCTCATGCA TTTGTTTAGG TTTTGCAACT ATGCCAACTA TGCCAAGTAA    2280

TGCTGCCCTA GTCTATTAGT TCATAGGGGC ATAAACACAG ATTTTACTTT GTGCTTACAT    2340

AAATGTTTTT TGCTCAGAAC TTGCAGTGGT ATTGGTCGTC TTAGACTTTT TGGCATGTGT    2400

TTGTTGTTGG AATATAATAT AAGTGAATTG TCAACCTTCT CCTATCAGCT TAAGCTTTTG    2460

GATAGAAAGA ATTGGTTGGT GCATGTAACT TAATATGGTA TTAAAGACAG AGGTCATGAA    2520

TTC                                                                  2523
```

(2) INFORMATION FOR SEQ ID NO:4:

(i) SEQUENCE CHARACTERISTICS:
        (A) LENGTH: 740 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:

(xi) SEQUENCE DESCRIPTION: SEQ ID NO:4:

```
Arg Pro Val Ala Glu Ala Val Gln Ala Glu Glu Asp Asp Asp Asp
  1               5                  10                  15

Asp Glu Glu Val Ala Glu Glu Arg Phe Ala Leu Gly Gly Ala Cys Arg
                 20                  25                  30

Val Leu Ala Gly Met Pro Ala Pro Leu Gly Ala Thr Ala Leu Arg Gly
         35                  40                  45

Gly Val Asn Phe Ala Val Tyr Ser Ser Gly Ala Ser Ala Ala Ser Leu
     50                  55                  60

Ser Leu Phe Ala Pro Gly Asp Leu Lys Ala Asp Arg Val Thr Glu Glu
 65                  70                  75                  80

Val Pro Leu Asp Pro Leu Leu Asn Arg Thr Gly Asn Val Trp His Val
                 85                  90                  95

Phe Ile His Gly Asp Glu Leu His Gly Met Leu Cys Gly Tyr Arg Phe
                100                 105                 110

Asp Gly Val Arg Ala Pro Glu Arg Gly Gln Tyr Tyr Asp Val Ser Asn
            115                 120                 125

Val Val Val Asp Pro Tyr Ala Lys Ala Val Val Ser Arg Gly Glu Tyr
        130                 135                 140

Gly Val Pro Ala Pro Gly Gly Ser Cys Trp Pro Gln Met Met Ile Pro
145                 150                 155                 160

Leu Pro Tyr Asn Lys Phe Asp Trp Gln Gly Asp Leu Pro Leu Gly Tyr
                165                 170                 175
```

```
His Gln Lys Asp Leu Val Ile Tyr Glu Met His Leu Arg Gly Phe Thr
            180                 185                 190

Lys His Asn Ser Ser Lys Thr Lys His Pro Gly Thr Tyr Ile Gly Ala
            195                 200                 205

Val Ser Lys Leu Asp His Leu Lys Glu Leu Gly Val Asn Cys Ile Glu
210                 215                 220

Leu Met Pro Cys His Glu Phe Asn Glu Leu Tyr Phe Ser Ser Ser
225                 230                 235                 240

Ser Lys Met Asn Phe Trp Gly Tyr Ser Thr Ile Asn Phe Phe Ser Pro
                245                 250                 255

Met Ala Arg Tyr Ser Ser Gly Ile Arg Asp Ser Gly Cys Gly Ala
            260                 265                 270

Ile Asn Glu Phe Lys Ala Phe Val Arg Glu Ala His Lys Arg Gly Ile
            275                 280                 285

Glu Val Ile Met Asp Val Val Phe Asn His Thr Ala Glu Gly Asn Glu
            290                 295                 300

Lys Gly Pro Ile Leu Ser Phe Arg Gly Ile Asp Asn Ser Thr Tyr Tyr
305                 310                 315                 320

Met Leu Ala Pro Lys Gly Glu Phe Tyr Asn Tyr Ser Gly Cys Gly Asn
                325                 330                 335

Thr Phe Asn Cys Asn His Pro Val Val Arg Glu Phe Ile Val Asp Cys
            340                 345                 350

Leu Arg Tyr Trp Val Thr Glu Met His Val Asp Gly Phe Arg Phe Asp
            355                 360                 365

Leu Ala Ser Ile Leu Thr Arg Gly Cys Ser Leu Trp Asp Pro Val Asn
370                 375                 380

Val Tyr Gly Glu Pro Met Glu Gly Asp Met Ile Thr Thr Gly Thr Pro
385                 390                 395                 400

Leu Val Ala Pro Pro Leu Ile Asp Met Ile Ser Asn Asp Pro Ile Leu
                405                 410                 415

Gly Asn Val Lys Leu Ile Ala Glu Ala Trp Asp Ala Gly Gly Leu Tyr
            420                 425                 430

Gln Glu Gly Gln Phe Pro His Trp His Val Trp Ser Glu Trp Asn Gly
            435                 440                 445

Lys Tyr Arg Asp Thr Val Arg Gln Phe Ile Lys Gly Thr Asp Gly Phe
450                 455                 460

Ala Gly Ala Phe Ala Glu Cys Leu Cys Gly Ser Pro Gln Leu Tyr Gln
465                 470                 475                 480

Ala Gly Gly Arg Lys Pro Trp His Ser Ile Gly Phe Val Cys Ala His
                485                 490                 495

Asp Gly Phe Thr Leu Ala Asp Leu Val Thr Tyr Asn Ser Lys Tyr Asn
            500                 505                 510

Leu Ser Asn Gly Glu Asp Phe Arg Asp Gly Glu Asn His Asn Leu Ser
            515                 520                 525

Trp Asn Cys Gly Glu Glu Gly Glu Phe Ala Ser Leu Ser Val Arg Arg
            530                 535                 540

Leu Arg Lys Arg Gln Met Arg Asn Phe Phe Val Cys Leu Met Val Ser
545                 550                 555                 560

Gln Gly Val Pro Met Phe Tyr Met Gly Asp Glu Tyr Gly His Thr Lys
                565                 570                 575

Gly Gly Asn Asn Asn Thr Tyr Cys His Asp His Tyr Val Asn Tyr Phe
            580                 585                 590

Arg Trp Asp Lys Lys Glu Glu Gln Ser Ser Asp Leu Tyr Arg Phe Cys
            595                 600                 605
```

```
Arg Leu Met Thr Glu Phe Arg Lys Glu Cys Glu Ser Leu Gly Leu Glu
    610                 615                 620

Asp Phe Pro Thr Ser Glu Arg Leu Lys Trp His Gly His Gln Pro Gly
625                 630                 635                 640

Lys Pro Asp Trp Ser Glu Ala Ser Arg Phe Val Ala Phe Thr Met Lys
                645                 650                 655

Asp Glu Thr Lys Gly Glu Ile Tyr Val Ala Phe Asn Thr Ser His Leu
            660                 665                 670

Pro Val Val Gly Leu Pro Glu Arg Ser Gly Phe Arg Trp Glu Pro
        675                 680                 685

Val Val Asp Thr Gly Lys Glu Ala Pro Tyr Asp Phe Leu Thr Asp Gly
    690                 695                 700

Leu Pro Asp Arg Ala Val Thr Val Tyr Gln Phe Ser His Phe Leu Asn
705                 710                 715                 720

Ser Asn Leu Tyr Pro Met Leu Ser Tyr Ser Ser Ile Ile Leu Val Leu
                725                 730                 735

Thr Pro Asp Val
            740
```

(2) INFORMATION FOR SEQ ID NO:5:

(i) SEQUENCE CHARACTERISTICS:
        (A) LENGTH: 772 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:

(xi) SEQUENCE DESCRIPTION: SEQ ID NO:5:

```
Met Lys Cys Pro Lys Ile Leu Gly Ala Leu Leu Gly Cys Ala Val Leu
1               5                   10                  15

Ala Gly Val Pro Ala Met Pro Ala His Ala Ala Ile Asn Ser Met Ser
                20                  25                  30

Leu Gly Ala Ser Tyr Asp Ala Gln Gln Ala Asn Ile Thr Phe Arg Val
            35                  40                  45

Tyr Ser Ser Gln Ala Thr Arg Ile Val Leu Tyr Leu Tyr Ser Ala Gly
50                  55                  60

Tyr Gly Val Gln Glu Ser Ala Thr Tyr Thr Leu Ser Pro Ala Gly Ser
65                  70                  75                  80

Gly Val Trp Ala Val Thr Val Pro Val Ser Ser Ile Lys Ala Ala Gly
                85                  90                  95

Ile Thr Gly Ala Val Tyr Tyr Gly Tyr Arg Ala Trp Gly Pro Asn Trp
            100                 105                 110

Pro Tyr Ala Ser Asn Trp Gly Lys Gly Ser Gln Ala Gly Cys Val Ser
        115                 120                 125

Asp Val Asp Ala Asn Gly Asp Arg Phe Asn Pro Asn Lys Leu Leu Leu
    130                 135                 140

Asp Pro Tyr Ala Gln Glu Asx Ser Gln Asp Pro Leu Asn Pro Ser Asn
145                 150                 155                 160

Gln Asn Gly Asn Val Phe Ala Ser Ala His Tyr Arg Thr Thr Asp Ser
```

-continued

```
                  165                 170                 175
Gly Ile Tyr Ala Pro Lys Gly Val Val Leu Val Pro Ser Thr Gln Ser
                180                 185                 190

Thr Gly Thr Lys Pro Thr Arg Ala Gln Lys Asp Asp Val Ile Tyr Glu
            195                 200                 205

Val His Val Arg Gly Phe Thr Glu Gln Asp Thr Ser Ile Pro Ala Gln
        210                 215                 220

Tyr Arg Gly Thr Tyr Tyr Gly Ala Gly Leu Lys Ala Ser Tyr Leu Ala
225                 230                 235                 240

Ser Leu Gly Val Thr Ala Val Glu Phe Leu Pro Val Gln Glu Thr Gln
                245                 250                 255

Asn Asp Ala Asn Asp Val Val Pro Asn Ser Asp Ala Asn Gln Asn Tyr
            260                 265                 270

Trp Gly Tyr Met Thr Glu Asn Tyr Phe Ser Pro Asp Arg Arg Tyr Ala
        275                 280                 285

Tyr Asn Lys Ala Ala Gly Gly Pro Thr Ala Glu Phe Gln Ala Met Val
    290                 295                 300

Gln Ala Phe His Asn Ala Gly Ile Lys Val Tyr Met Asp Val Val Tyr
305                 310                 315                 320

Asn His Thr Ala Glu Gly Gly Thr Trp Thr Ser Ser Asp Pro Thr Thr
                325                 330                 335

Ala Thr Ile Tyr Ser Trp Arg Gly Leu Asp Asn Ala Thr Tyr Tyr Glu
            340                 345                 350

Leu Thr Ser Gly Asn Gln Tyr Phe Tyr Asp Asn Thr Gly Ile Gly Ala
        355                 360                 365

Asn Phe Asn Thr Tyr Asn Thr Val Ala Gln Asn Leu Ile Val Asp Ser
    370                 375                 380

Val Ala Tyr Trp Ala Asn Thr Met Gly Val Asp Gly Phe Arg Phe Asp
385                 390                 395                 400

Leu Ala Ser Val Leu Gly Asn Ser Cys Leu Asn Ala Val His Ala Ser
                405                 410                 415

Ala Pro Asn Cys Pro Asn Gly Gly Tyr Asn Phe Asp Ala Ala Asp Ser
            420                 425                 430

Asn Val Ala Ile Asn Arg Ile Leu Arg Glu Phe Thr Val Arg Pro Ala
        435                 440                 445

Ala Gly Gly Thr Val Trp Ile Cys Leu Arg Asn Leu Gly Pro Ser Ala
    450                 455                 460

Ala Thr Arg Thr Ser Trp Val Asp Ser Arg Val Val Arg Val Glu
465                 470                 475                 480

Trp Ser Val Pro Arg Gln Leu Arg Gln Ala Gln Asn Glu Leu Gly Ser
                485                 490                 495

Met Thr Ile Tyr Val Thr Gln Asp Ala Asn Asp Phe Ser Gly Ser Ser
            500                 505                 510

Asn Leu Phe Gln Ser Ser Gly Arg Ser Pro Trp Asn Ser Ile Asn Phe
        515                 520                 525

Ile Asp Val His Asp Gly Met Thr Leu Lys Asp Val Tyr Ser Cys Asn
    530                 535                 540

Gly Ala Asn Asn Ser Gln Ala Ser Tyr Gly Pro Ser Asp Gly Gly Thr
545                 550                 555                 560

Ser Thr Asn Tyr Ser Trp Asp Gln Gly Met Ser Ala Gly Thr Gly Ala
                565                 570                 575

Ala Val Asp Gln Arg Arg Ala Ala Arg Thr Gly Met Ala Phe Glu Met
            580                 585                 590
```

```
Leu Ser Ala Gly Thr Pro Leu Met Gln Gly Gly Asp Glu Tyr Leu Arg
        595                 600                 605
Thr Leu Gln Cys Asn Asn Ala Tyr Asn Leu Asp Ser Ser Ala Asn
610                 615                 620
Trp Leu Thr Tyr Ser Trp Thr Thr Asp Gln Ser Asn Phe Tyr Thr Phe
625                 630                 635                 640
Ala Gln Arg Leu Ile Arg Ser Ala Arg His Ile Pro Leu Arg Pro Ser
                645                 650                 655
Ser Trp Tyr Ser Gly Ser Gln Leu Thr Trp Tyr Gln Pro Ser Gly Ala
                660                 665                 670
Val Ala Asp Ser Asn Tyr Trp Asn Asn Thr Ser Asn Tyr Ala Ile Ala
                675                 680                 685
Tyr Ala Ile Asn Gly Pro Ser Leu Gly Asp Ser Asn Asp Ser Ile Tyr
        690                 695                 700
Val Ala Tyr Asn Gly Trp Ser Ser Val Thr Phe Thr Leu Pro Ala
705                 710                 715                 720
Pro Pro Ser Gly Thr Gln Trp Tyr Arg Val Thr Asp Thr Cys Asp Trp
                725                 730                 735
Asn Asp Gly Ala Ser Thr Phe Val Ala Pro Gly Ser Glu Thr Leu Ile
                740                 745                 750
Gly Gly Ala Gly Thr Thr Tyr Gly Gln Cys Gly Gln Ser Leu Leu Leu
                755                 760                 765
Leu Ile Ser Lys
        770
```

(2) INFORMATION FOR SEQ ID NO:6:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:6:

GTATGTACTA TTATCTATCC C                                21

(2) INFORMATION FOR SEQ ID NO:7:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:7:

-continued

```
GGGATCATAC CAGCCATTTG A                                        21

(2) INFORMATION FOR SEQ ID NO:8:

(i) SEQUENCE CHARACTERISTICS:
          (A) LENGTH: 15 base pairs
          (B) TYPE: nucleic acid
          (C) STRANDEDNESS: single
          (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:8:

GGCTGTCGCG TGCGT                                               15

(2) INFORMATION FOR SEQ ID NO:9:

(i) SEQUENCE CHARACTERISTICS:
          (A) LENGTH: 15 base pairs
          (B) TYPE: nucleic acid
          (C) STRANDEDNESS: single
          (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:9:

GCGTACGTCT CTAAA                                               15
```